(12) United States Patent
Pereira et al.

(10) Patent No.: US 10,219,829 B2
(45) Date of Patent: Mar. 5, 2019

(54) REUSABLE DELIVERY DEVICES

(71) Applicant: Boston Scientific Scimed, Inc., Maple Grove, MN (US)

(72) Inventors: Peter J. Pereira, Mendon, MA (US); Kenneth W. Adams, Wilmington, MA (US); Michael S. H. Chu, Brookline, MA (US); John Goncalves, New Bedford, MA (US); Sharmad S. Joshi, Newton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 265 days.

(21) Appl. No.: 14/850,511

(22) Filed: Sep. 10, 2015

(65) Prior Publication Data

US 2016/0074147 A1     Mar. 17, 2016

Related U.S. Application Data

(60) Provisional application No. 62/049,601, filed on Sep. 12, 2014.

(51) Int. Cl.
| A61B 17/00 | (2006.01) |
| A61F 2/00  | (2006.01) |
| A61B 17/34 | (2006.01) |
| A61B 17/06 | (2006.01) |

(52) U.S. Cl.
CPC .... *A61B 17/3403* (2013.01); *A61B 17/06109* (2013.01); *A61B 17/3417* (2013.01); *A61B 17/3421* (2013.01); *A61B 17/3468* (2013.01); *A61B 2017/00477* (2013.01); *A61B 2017/00805* (2013.01); *A61F 2/0045* (2013.01)

(58) Field of Classification Search
CPC .. A61B 2017/00805; A61B 2017/3405; A61B 17/3403; A61B 17/3417; A61B 17/3468; A61F 2002/0072
See application file for complete search history.

(56) References Cited

U.S. PATENT DOCUMENTS

2005/0131392 A1* 6/2005 Chu ................. A61B 17/00234
                                                      606/1
2008/0097342 A1* 4/2008 Gordin ............... A61M 5/3216
                                                      604/263

(Continued)

*Primary Examiner* — Thaddeus B Cox
(74) *Attorney, Agent, or Firm* — Brake Hughes Bellermann LLP

(57) ABSTRACT

According to an aspect, a medical device includes a needle member having a curved portion, a handle coupled to the needle member, and a pusher member including a sheath and an extension member. The sheath may be bendable. The extension member is configured to be slidably coupled to a track of the handle such that extension member slides within the track during a medical procedure. The sheath defines a lumen configured to receive a portion of the needle member. The extension member is configured to be de-coupled from the track of the handle after the medical procedure. The sheath is configured to be de-coupled from the needle member after the medical procedure. In some examples, the sheath of the pusher member is configured to bend to conform to the curved portion when the sheath of the pusher member is moved over the curved portion of the needle member.

19 Claims, 23 Drawing Sheets

(56) References Cited

U.S. PATENT DOCUMENTS

| | | | |
|---|---|---|---|
| 2010/0274074 A1* | 10/2010 | Khamis | A61B 17/00234 600/37 |
| 2012/0130282 A1* | 5/2012 | Galloway | A61B 17/3403 600/587 |
| 2014/0025036 A1* | 1/2014 | Bierman | A61M 25/0097 604/506 |
| 2014/0062113 A1* | 3/2014 | Kovarik | A47F 13/06 294/198 |

* cited by examiner

REUSABLE DELIVERY DEVICES

CROSS-REFERENCE TO RELATED APPLICATION

This application is a Nonprovisional of, and claims priority to, U.S. Patent Application No. 62/049,601, filed on Sep. 12, 2014, entitled "REUSABLE DELIVERY DEVICES", which is incorporated by reference herein in its entirety.

TECHNICAL FIELD

This disclosure relates generally to medical devices, surgical procedures, and techniques for assembling and disassembling the medical devices, and particularly reusable medical devices for delivering implants, and methods of assembling and disassembling the reusable medical devices.

BACKGROUND

Most conventional sling delivery devices are designed for single-use. For example, after a delivery device is used within a surgical procedure for implanting a sling, the single-use sling delivery device is discarded. During the surgical procedure, bodily fluids or other contaminating substances may be embedded within components or between components of the delivery device, which may be relatively difficult to clean and sterilize. In particular, conventional sling delivery devices may be constructed in a manner that does not permit its components to be easily disassembled, properly sterilized, and then re-assembled to be used in a subsequent surgical procedure. As such, the re-processing of single-use sling deliver devices may pose health and safety hazards to the patient and the operator. However, despite these hazards, the re-processing of single-use sling delivery devices may be relatively common in certain parts of the world.

SUMMARY

According to an aspect, a medical device includes a needle member having a curved portion, a handle coupled to the needle member, and a pusher member including a sheath and an extension member. In some examples, the sheath is bendable. The extension member is configured to be slidably coupled to a track of the handle such that extension member slides within the track during a medical procedure. The sheath defines a lumen configured to receive a portion of the needle member. The extension member is configured to be de-coupled from the track of the handle after the medical procedure. The sheath is configured to be de-coupled from the needle member after the medical procedure. In some examples, the sheath of the pusher member is configured to bend to conform to the curved portion when the sheath of the pusher member is moved over the curved portion of the needle member.

The medical device may include one or more of the following features (or any combination thereof). The medical device may include a protrusion component configured to be coupled to the handle. The protrusion component is configured to limit movement of the pusher member in relation to the handle during the medical procedure. In some examples, the protrusion component may include an insert having a base and a flexible projection that extends from the base. The insert is configured to be inserted into a slot of the handle such that, when inserted, the flexible projection protrudes into the track of the handle. In some examples, the protrusion component includes an insert having a flexible projection, where the insert is coupled to the track of the handle. In some examples, the protrusion component includes a removable pin, and the handle defines a through-hole configured to receive the removable pin such that a portion of the removable pin protrudes into the track of the handle. In some examples, the protrusion component includes an adjustable pin assembly including a modified pin and a spring-loaded detent. The extension member may define a slot. The extension member may define an enlarged portion of a proximal end of the extension member. The bendable shaft may define a plurality of recesses.

According to an aspect, a method for enabling reuse of a medical device having a pusher member, a needle member, and a handle includes decoupling an extension member of the pusher member from a track of the handle after a medical procedure, decoupling the pusher member from the needle member, and sterilizing the pusher member, the needle member, and the handle.

The method may include one or more of the following features (or any combination thereof). The handle may include a protrusion disposed within the track of the handle configured to limit distal movement of the pusher member during the surgical procedure. In some examples, the decoupling the extension member of the pusher member from the track of the handle may include applying greater distal force to the extension member than applied during the medical procedure to slide the extension member past the protrusion. In some examples, the decoupling the extension member of the pusher member from the track of the handle may include moving the protrusion such that the protrusion does not extend within the track of the handle and moving the pusher member in a distal direction such that the extension member is not disposed with the track of the handle. In some examples, the decoupling the pusher member from the needle member may include sliding the pusher member over a curved portion of the needle member such that a bendable sheath of the pusher member conforms to a curvature of the curved portion of the needle member. In some examples, the pusher member defines a slot extending along a longitudinal axis of the pusher member, and the needle member includes a curved portion. The decoupling the pusher member from the needle member may include decoupling the pusher member from the needle member via the slot. The method may further include coupling the pusher member to the needle member by sliding a distal end portion of the needle member into a lumen of the pusher member, and coupling the extension member of the pusher member to the track of the handle such that the extension member can slide within the track of the handle.

According to an aspect, a medical device may include a needle member, a handle coupled to the needle member, and a pusher member including a sheath and an extension member. The extension member is configured to be slidably coupled to a track of the handle such that extension member slides within the track during a medical procedure. The sheath defines a lumen configured to receive a portion of the needle member. The pusher member is configured to be de-coupled from the handle. The medical device includes a protrusion component configured to be coupled to the track of the handle. The protrusion component is configured to protrude into the track of the handle such that a travel distance of the pusher member is limited.

The medical device may include one or more of the following features (or any combination thereof). The needle member may include a curved portion, and sheath may be bendable such that the sheath is configured to bend over the curved portion of the needle member when decoupling the pusher member from the needle member. The pusher member may define a slot such that the pusher member is configured to be de-coupled from the needle member via the slot. In some examples, the protrusion component may include an insert having a base and a flexible projection that extends from the base. The insert may be configured to be inserted into a slot of the handle such that, when inserted, the flexible projection protrudes into the track of the handle. In some examples, the protrusion component may include an insert having a flexible projection, where the insert is coupled to the track of the handle. In some examples, the protrusion component may include a removable pin, and the handle may define a through-hole configured to receive the removable pin such that a portion of the removable pin protrudes into the track of the handle. In some examples, the protrusion component is adjustable between a first semi-locked position and a second semi-locked position. In some examples, the extension member defines a slot.

According to an aspect, a medical device may include a needle member, a handle coupled to the needle member, and a pusher member including a sheath and an extension member. The extension member is configured to be slidably coupled to a track of the handle such that extension member slides within the track during a medical procedure. The sheath defines a lumen configured to receive a portion of the needle member. The pusher member is configured to be de-coupled from the handle. The pusher member is configured to be de-coupled from the handle. The medical device includes a protrusion component configured to be coupled to the track of the handle. The protrusion includes an insert configured to be inserted into a slot of the handle such that, when inserted, the insert is configured to protrude into the track of the handle to limit a travel distance of the pusher member. In some examples, the insert is removable after the medical procedure. In other examples, the insert is not removable after the medical procedure.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

The term patient may hereafter be used for a person who benefits from the medical device or the methods disclosed in the present application. For example, the patient can be a person whose body is operated through the medical device or the method disclosed by the present invention. For example, in some aspects, the patient may be a human female, a human male, or any other mammal.

The terms proximal and distal described in relation to various devices, apparatuses, and components as discussed in the subsequent text of the present application are referred with a point of reference. The point of reference, as used in this description, is a perspective of an operator. The operator may be a surgeon, a physician, a nurse, a doctor, a technician, and the like who may perform the procedure and operate the medical device as described in the present invention. The term proximal refers to an area or portion that is closer or closest to the operator during a surgical procedure. The term distal refers to an area or portion that is farther or farthest from the operator.

Figure 1A:
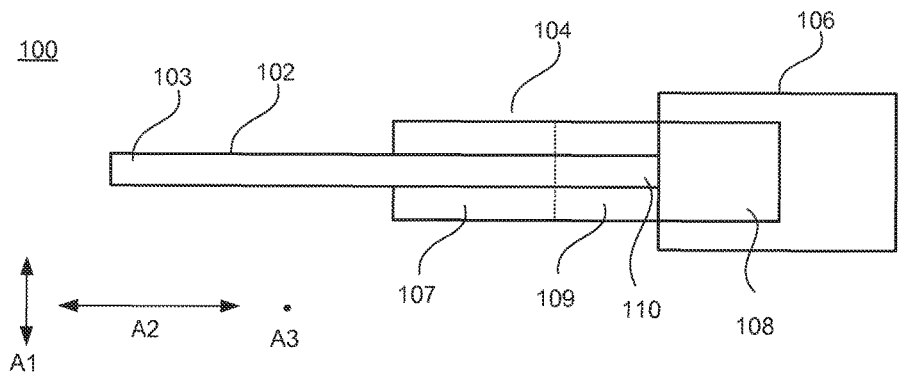
FIG. 1A illustrates a medical device having a pusher member within a retracted configuration in relation to a handle.
Figure 1B:
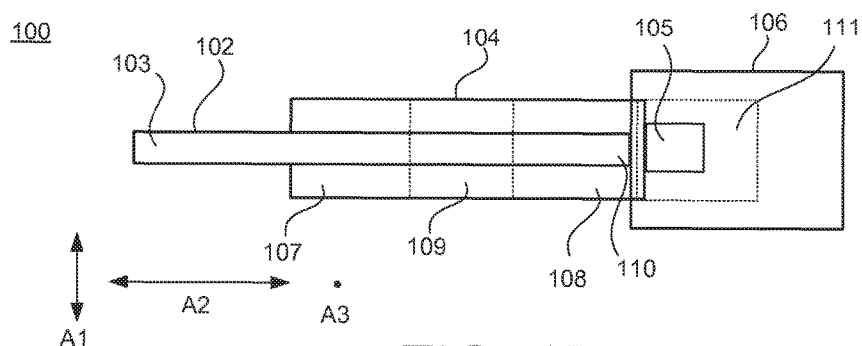
FIG. 1B illustrates the pusher member within an extended configuration in relation to the handle.
Figure 1C:
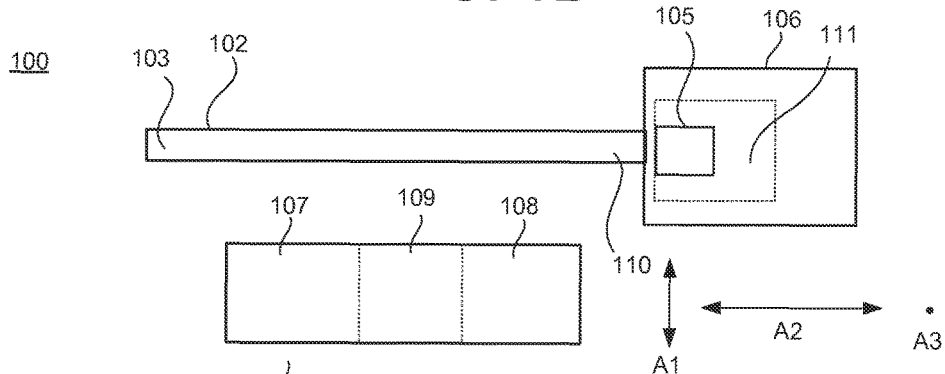
FIG. 1C illustrates the pusher member decoupled from both the handle and needle member.

FIGS. 1A-1C illustrate a medical device 100 having a needle member 102, a handle 106 coupled to the needle member 102, and a pusher member 104 removably coupled to the handle 106 and the needle member 102 according to various aspects. The medical device 100 may be a delivery device for the delivery of implants (e.g., slings, graphs, etc.) into the body of the patient. In some examples, the medical device 100 may be used to delivery mid-urethral slings into the body of the patient. The features described in FIGS. 1A-1C may be extended to any of the implementations described with reference to the other figures.

FIG. 1A illustrates the pusher member 104 within a retracted configuration in relation to the handle 106 according to an aspect. FIG. 1B illustrates the pusher member 104 within an extended configuration in relation to the handle 106 according to an aspect. FIG. 1C illustrates the pusher member 104 decoupled from both the handle 106 and the needle member 102. The pusher member 104 may be configured to slide along an axis A2 from the retracted position (e.g., FIG. 1A) to the extended position (e.g., FIG. 1B) (or any position between the retracted position and the extended position) during the surgical procedure. The pusher member 104 can push an anchor or other implant off the needle member 102 during the surgical procedure. In order to enable re-use of the medical device 100, the medical device 100 may be dis-assembled and assembled. In some aspects, the pusher member 104 may be decoupled from the handle 106 and the needle member 102 (e.g., FIG. 1C) so that the pusher member 104 can be cleaned and sterilized, and then re-assembled for a subsequent surgical procedure. In some aspects, the pusher member 104 can be discarded, and a new pusher member 104 can be re-assembled with the other components of the medical device 100.

The pusher member 104 may define a lumen configured to receive portions of the needle member 102. Referring to FIGS. 1A-1B, the pusher member 104 may be slidably coupled to the handle 106 such that the pusher member 104 slides relative to the handle 106 during a surgical procedure. During the surgical procedure, the pusher member 104 may distally slide along a portion of the needle member 102 along the axis A2 to assist with the delivery of the implant or sling. However, after the surgical procedure, the pusher member 104 may be de-coupled from both the handle 106 and the needle member 102 so that these components can be sterilized and then re-assembled to be re-used in a subsequent medical procedure. In particular, the pusher member 104 (e.g., the lumen of the pusher member 104) can be separated in order to be cleaned and sterilized since this component is relatively difficult to clean if fixedly coupled to the handle 106 and/or the needle member 102. The axis A2 may be parallel to a longitudinal axis of the medical device 100. In some examples, the axis A2 may be the central axis of the needle member 102. An axis A1 may be perpendicular to the axis A2. An axis A3 into the page (shown as a dot) is orthogonal to the axes A1 and A2. The axes A1, A2, and A3 may be used throughout several of the various views of the implementations described throughout the figures.

The needle member 102 may be an elongated cylindrical structure. The needle member 102 may include one or more curved portions in two or three dimensional planes. In other examples, the needle member 102 may be substantially straight. In other examples, the needle member 102 may include one or more bent portions in two or three dimensional planes. The needle member 102 may include portions having different diameters such as a reduced diameter portion. In some examples, the needle member 102 may include portions having a non-cylindrical structure such as a D-shaped structure. The needle member 102 may include a metal or metal-based material such as stainless steel. The needle member 102 may define a lumen. In other examples, the needle member 102 may be solid (e.g., without a lumen).

The needle member 102 may include a distal end portion 103 and a proximal end portion 110. The distal end portion 103 of the needle member 102 may be configured to pierce or penetrate bodily tissue when inserted into the body. The distal end portion 103 of the needle member 102 may be a sharp tip portion. In other examples, the distal end portion 103 of the needle member 102 may be a blunt tip portion or a round tip portion. In some examples, the distal end portion 103 of the needle member 102 may include a coupling member configured to couple an implant to the needle member 102. In particular, the distal end portion 103 of the needle member 102 may define a slot (e.g., L-shaped slot) configured to couple an implant to the needle member 102.

The proximal end portion 110 of the needle member 102 may be coupled to the handle 106. In some examples, the proximal end portion 110 of the needle member 102 may be fixedly coupled to the handle 106. The proximal end portion 110 of the needle member 102 may be coupled to the handle 106 using an adhesive or bonding material. In some examples, the proximal end portion 110 of the needle member 102 may include a threaded (male or female) portion such that the threaded male portion is inserted into a threaded (male or female) portion of the handle 106, and the threaded portions are secured using an adhesive or bonding material. However, any medical device described herein may encompass any type of coupling mechanism to securely couple the handle 106 to the proximal end portion 110 of the needle member 102. In other examples, the proximal end portion 110 of the needle member 102 may be removably coupled to the handle 106 such that the needle member 102 and the handle 106 may be de-coupled, and thereby cleaned separately. For example, the proximal end portion 110 may include a threaded male (or female) portion such that the threaded male (or female) portion is coupled to a threaded female (or male) portion of the handle 106. Also, any type of coupling mechanism may be used to removably couple the needle member 102 to the proximal end portion 110 of the handle 106.

In some examples, the pusher member 104 may be a bendable pusher. For example, the pusher member 104 may include one or more portions that are bendable such that the bendable portions conform to a shape of the needle member 102 as the needle member 102 slides through the lumen of the pusher member 104. In this manner, the pusher member 104 may be disassembled and assembled with a curved or bent needle member 102. For assembling the medical device 100, the pusher member 104 may be slide over the distal end portion 103 of the needle member 102 towards the proximal end portion 110 of the needle member 102, and the bendable portions of the pusher member 104 may conform to the curvature of the needle member 102, thereby permitting the pusher member 104 to slide over the curved or bent portions of the needle member 102. Then, the pusher member 104 may be coupled to the handle 106. For disassembling the medical device 100, the pusher member 104 may be decoupled from the handle 106. Then, the pusher member 104 may move towards the distal end portion 103 of the needle member 102 such that the bendable portions of the pusher member 104 conform to the shape of the needle member 102, thereby permitting the pusher member 104 to slide over the curved or bent portions of the needle member 102. Further examples of the bendable pusher member 104 are further discussed with reference to FIGS. 2A-2C, 3A-3B, and 4.

In other examples, the pusher member 104 is relatively rigid. In order to permit the removability of a relatively rigid pusher member 104 with respect to a curved or bent needle member 102, the pusher member 104 may define a slot that is parallel to the lumen (e.g., extends in the direction A2) that permits the pusher member 104 to be removed from the handle 106 from its side. The details of the slot of the pusher member 104 are further described later in the disclosure.

The pusher member 104 may include a sheath 107, a handle portion 109, and an extension member 108. The sheath 107 may have a length larger than a combined length of the handle portion 109 and the extension member 108. The handle portion 109 may have a structure configured to be grasped by an operator of the medical device 100. For example, an operator may grasp the handle portion 109 of the pusher member 104 and the handle 106 to slide the pusher member 104 during the surgical procedure. The extension member 108 proximally extends from the handle portion 109 along the axis A2 (e.g., extends from a top or bottom surface of the handle portion 109) and is slidably coupled to the handle 106. In some examples, the extension member 108 may be semi-flexible such that the extension member 108 may bend when force is applied to the extension member 108.

The sheath 107 and the handle portion 109 of the pusher member 104 may define the lumen of the pusher member 104 such that the needle member 102 slides through the lumen of the sheath 107 and the handle portion 109. In some examples, the sheath 107 and the handle portion 109 may define the slot of the pusher member 104. For example, the slot may be parallel to the lumen (e.g., extends in the direction A2) that permits the pusher member 104 to be removed from the handle 106 in any direction orthogonal to the axis A2 (e.g. from a side of the pusher member 104). The slot of the sheath 107 and the handle portion 109 may have a depth such that it extends into the lumen (e.g., along the axis A3) and a length such that it extends along the entire length of the sheath 107 and the handle portion 109 along the axis A2. The slot may permit the pusher member 104 to be decoupled from the needle member 102 by moving the pusher member 104 in any direction orthogonal to the axis A2. Further examples of the slot on the pusher member 104 are described with reference to FIGS. 6A, 8A-8B, and 9C-9D. In other examples, the sheath 107 and the handle portion 109 do not define the slot, e.g., the sheath 107 and the handle portion 109 fully surround outer surfaces of portions of the needle member 102. Further examples of the pusher member 104 without the slot are described with reference to FIGS. 2A-2C, 3A-3B, and 4.

The sheath 107, the handle portion 109, and the extension member 108 may define different shapes or structures. In some examples, the sheath 107, the handle portion 109, and/or the extension member 108 may be unitarily formed. In other examples, the sheath 107, the handle portion 109, and/or the extension member 108 may be separately formed and coupled together. Also, the sheath 107, the handle portion 109, and the extension member 108 may be made from the same or similar type of materials or different materials.

In some examples, the sheath 107 may be bendable. In some examples, the entire sheath 107 may be bendable. The sheath 107, the handle portion 109, and the extension member 108 may be a unitary or single plastic-based component, however the sheath 107 may be flexible or bendable while the handle portion 109 and the extension member 108 are relatively rigid or less flexible than the sheath 107. For example, the sheath 107 may include a plurality of recesses disposed along a length of the sheath 107. The plurality of recesses is defined on the outer surface of the sheath 107. The recesses may be considered slots, openings, grooves, or cut-out portions that are distributed along the length of the sheath 107. The recesses may permit the bendability of the sheath 107. In some examples, the sheath 107 may have a D-shaped configuration defining a rounded outer surface and a flat outer surface. In some example, the plurality of recesses may be defined by the rounded outer surface along a length (or a portion thereof) of the sheath 107 while the flat outer surface is relatively smooth (e.g., without any recesses). However, the sheath 107 may have other types of shapes including cylindrical or tubular, and the plurality of recesses may be defined at various portions of the outer surface of the sheath 107. Further examples of the bendable sheath 107 having the recesses are described with reference to FIGS. 2A-2C and 3A-3B.

In other examples, the sheath 107 may be a flexible tube. For example, the flexible tube may not define the recesses, but rather the material of the flexible tube permits the bendability of the sheath 107. The flexible tube may be formed from a relatively flexible plastic-based material. In some examples, the flexible tube may be formed from polyethylene. In some examples, the handle portion 109 and the extension member 108 may be composed of a unitary plastic-based component, and the sheath 107 including the flexible tube is coupled to the unitary plastic component of the handle portion 109 and the extension member 108. Further examples of the flexible tube as the sheath 107 are discussed with reference to FIG. 4. When the sheath 107 is bendable, the above-described slot of the pusher member 104 is not needed since the pusher member 104 can slide over the curved or bent portions of the needle member 102.

Referring to FIGS. 1B-1C, the handle 106 may define a track 111 that is shaped to receive the extension member 108 of the pusher member 104 and allow the extension member 108 to slide along the track 111 during the surgical procedure. The track 111 may include a recess from a surface of the handle 106. For example, the handle 106 may define the recess from a top surface of the handle 106 with a coupling feature that allows the extension member 108 to slide along the length of the recess while keeping the extension member 108 within the recess. The handle 106 may have any type of structure having a rear face (rear surface), front face (front surface), top face (top surface), bottom face (bottom surface). The rear face is opposite to the front face. The top face is opposite to the bottom face. The terms rear, front, top, and bottom are from the perspective of the track 111 of the handle 106 facing upwards and the front face directed towards the distal direction. As such, although the orientation of the handle 106 may change during the surgical procedure and the assembling/disassembling of the medical device, these terms may be used for ease of describing the various components discussed herein.

Also, the medical device 100 may include a protrusion component 105 that is coupled to the handle 106 and configured to limit the travel distance of pusher member 104 during the surgical procedure. However, when the protrusion component 105 and/or the pusher member 104 is manipulated, the pusher member 104 may be decoupled from the track 111 of the handle 106. When coupled to the handle 106, the protrusion component 105 is configured to extend into the recess of the track 111 to limit the travel of the pusher member 104 during the surgical procedure. When the pusher member 104 moves from its retracted position (FIG. 1A) to its extended position (FIG. 1B) during the surgical procedure, portions of the extension member 108 slides past the protrusion component 105 until features on the extension member 108 engage with the protrusion component 105, thereby limiting the distal movement along the axis A2 of the pusher member 104 during the surgical procedure.

In some examples, the protrusion component 105 may be removeably coupled to the handle 106. In some examples, when inserted or coupled to the handle 106, the protrusion component 105 is securely fixed to the handle 106 (e.g., not removable). In some examples, when inserted or coupled to the handle 106, the protrusion component 105 is adjustable in the sense that the protrusion component 105 can be manipulated to allow the pusher member 104 to be decoupled from the handle 106 (e.g., either extending into the recess of the track 111 or not extending into the recess of the track 111).

In some examples, the protrusion component 105 may include an insert having a base and a flexible projection. The flexible projection extends from a surface of the base, and is bendable towards (and away) from the surface of the base. In this example, the handle 106 may define a slot (e.g., a T-shaped slot) on the front face of the handle 106, when assembling the medical device 100, the base of the insert is inserted into the slot of the handle 106 in the proximal direction along the axis A2. In some examples, the insert is permanently fixed to the handle 106 such that the insert is not removable after the insert is inserted into the slot of the handle 106. In other examples, the insert is not permanently fixed to the handle 106 where the fit of the insert to the slot of the handle 106 is designed such that the insert remains in position within the slot of the handle 106 during the surgical procedure, but with more substantial force, the insert may be removed from the slot of the handle 106 after the surgical procedure to be subsequently cleaned and later re-inserted back into the handle 106 for the next surgical procedure.

When inserted, the flexible projection of the insert springs outwardly from the base into the recess of the track 111 to limit the travel of the pusher member 104. In some examples, the base and the flexible projection may be a molded or stamped sheet metal component (base) that contains a tongue (flexible projection) that is sprung outwardly. After the medical procedure, when disassembling the medical device 100, the pusher member 104 may be moved to its extended position (FIG. 1B). Then, the flexible projection may be depressed inwardly towards the base by a user so that the extension member 108 can slide past the distal tip portion of the flexible projection, thereby decoupling the pusher member 104 from the handle 106. Next, the pusher member 104 can be removed from the needle member 102 and cleaned separately from the other components of the medical device 100 so that the hard-to-reach areas (e.g., the lumen of the pusher member 104) can be easily accessed for effective cleaning and sterilization in preparation for a subsequent surgical procedure. For example, in the example of a curved or bent needle member 102, if the sheath 107 is flexible, the pusher member 104 may be decoupled from the needle member 102 by sliding the pusher member 104 over the distal end portion 103 of the needle member 102. If the sheath 107 is relatively rigid, the pusher member 104 may be decoupled from the needle member 102 via the slot on the pusher member 104. Further examples of the base and the flexible projection as the protrusion component 105 are described with reference to FIGS. 6A-6E.

In other examples, the protrusion component 105 includes the flexible projection but not the base. Also, rather than being inserted into the slot of the handle 106, the flexible projection is coupled within the recess of the track 111. For example, the flexible projection may be coupled to the handle 106 within the recess of the track 111. In some examples, the flexible projection may be coupled within the recess of the track 111 using a hole and boss coupling mechanism. For example, the flexible projection may define the hole, and the boss is coupled to the lowered surface of the recess of the track 111 and extends outwardly from the lowered surface of the recess. The fit between the hole and the boss may be designed to create a permanent assembly or semi-permanent assembly such that the flexible projection remains coupled to the handle 106 during the surgical procedure, but may be disassembled by the user with more substantial force. Further examples of the flexible projection without the base are described with reference to FIG. 7.

In other examples, the protrusion component 105 includes an adjustable and/or removable pin. For example, the handle 106 may define a through-hole from the top face of the handle 106 to the bottom face of the handle 106. The pin may be inserted from the top face of the handle 106 and may extend through the handle 106 such that a portion of the pin extends into the recess of track 111 on the bottom face, and this portion of the pin limits the travel distance of the pusher member 104 and prevents it from being disassembled. In some examples, the pin may include a threaded screw, and the through-hole of the handle 106 includes grooves configured to engage with the threaded screw. For re-use of the medical device 100, the pin may be removed (e.g., unscrewed) and the pusher member 104 may be coupled from the handle 106, and then decoupled from the needle member 102. Further examples of the pin as the protrusion component 105 are described with reference to FIGS. 8A-8F.

In other examples, the pin may be included as part of an adjustable pin assembly. The adjustable pin assembly may include a modified pin and a spring-loaded detent. The modified pin may include two reduced diameter portions that are spaced apart by a distance. In some examples, the spring-loaded detent may be a spring loaded ball detent. The handle 106 may define a cavity on the rear surface of the handle 106, and the spring-loaded detent may be inserted from the rear surface of the handle 106 in the distal direction along the axis A2. Also, the handle 106 may define a through-hole from the top surface of the handle 106 to the bottom face of the handle 106. The modified pin may be inserted into the through-hole of the handle 106 such that the spring-loaded detent and the modified pin are perpendicular to each other. The interaction of the spring-loaded detent and the modified pin may provide the modified pin with a first semi-locked position and a second semi-locked position. The modified pin may be moved between the first semi-locked position and the second semi-locked position. The first semi-locked position may be the position used during the surgical procedure, e.g., to limit the travel distance of the pusher member 104. The second semi-locked position may permit the pusher member 104 to be decoupled from the handle 106. Further examples of the adjustable pin assembly as the protrusion component 105 are described with reference to FIGS. 9A-9D, 10-12, and 13A-13B.

Figure 2A:
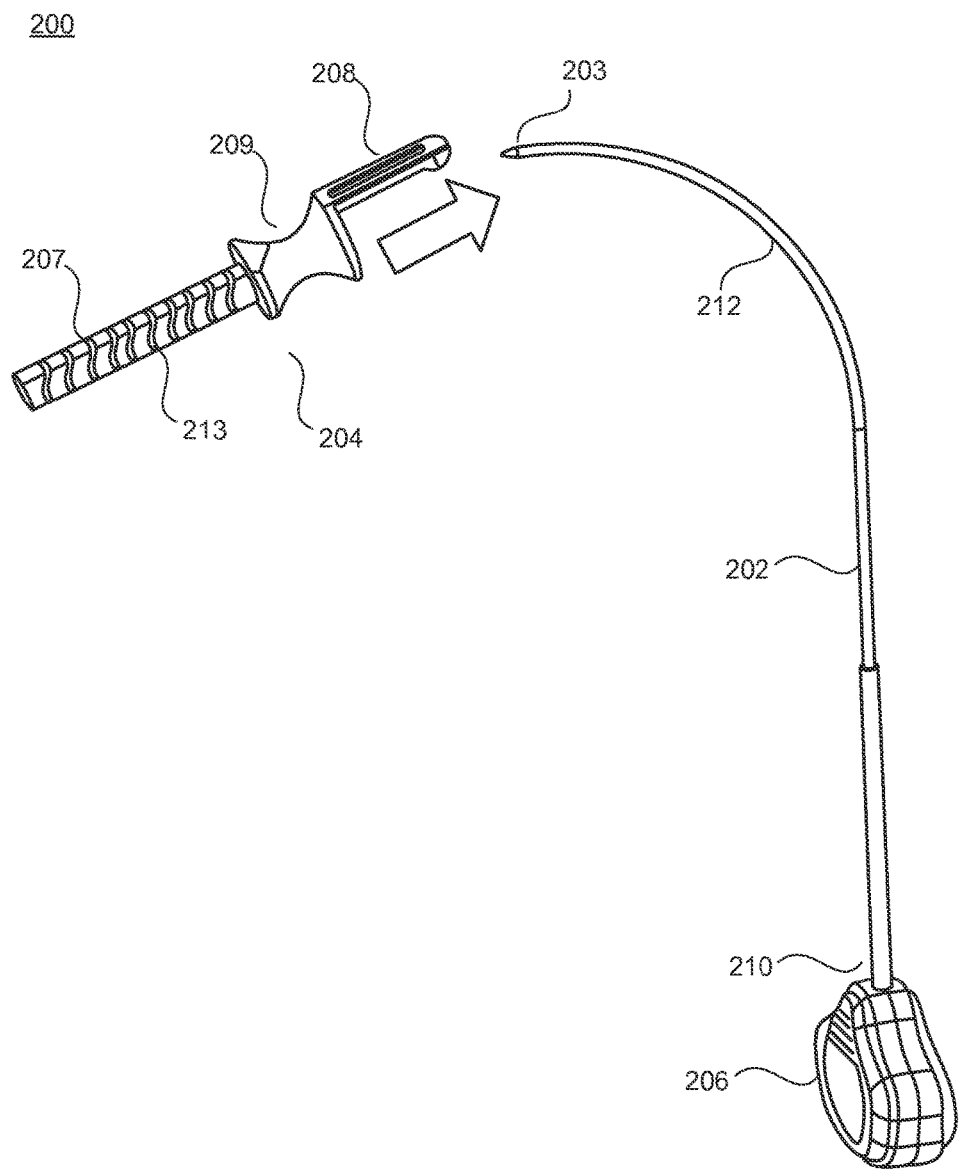
FIG. 2A illustrates a perspective of a pusher member that is configured to slide onto a needle member.
Figure 2B:
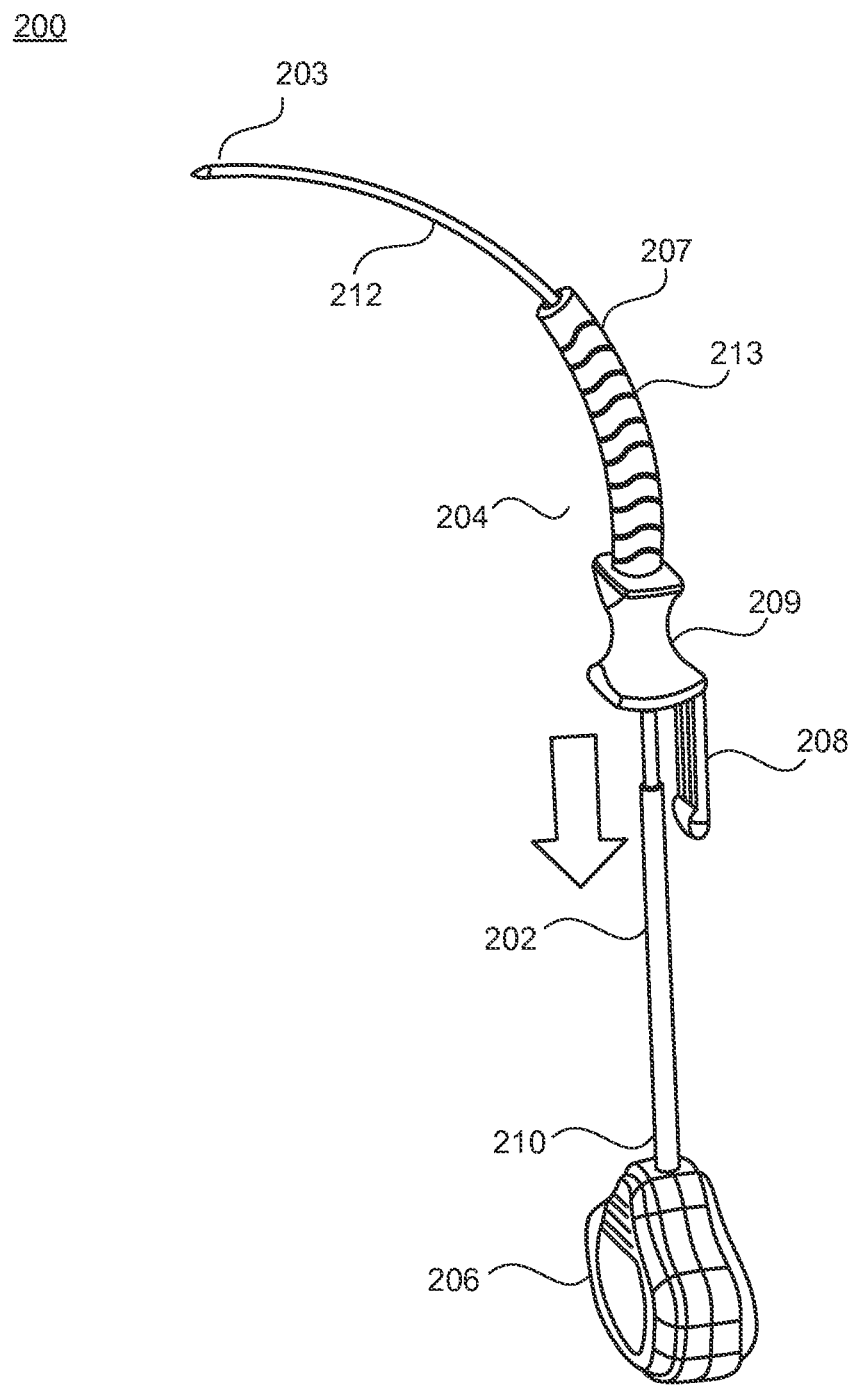
FIG. 2B illustrates a bendable portion of the pusher member conforming to the shape of the needle member.
Figure 2C:
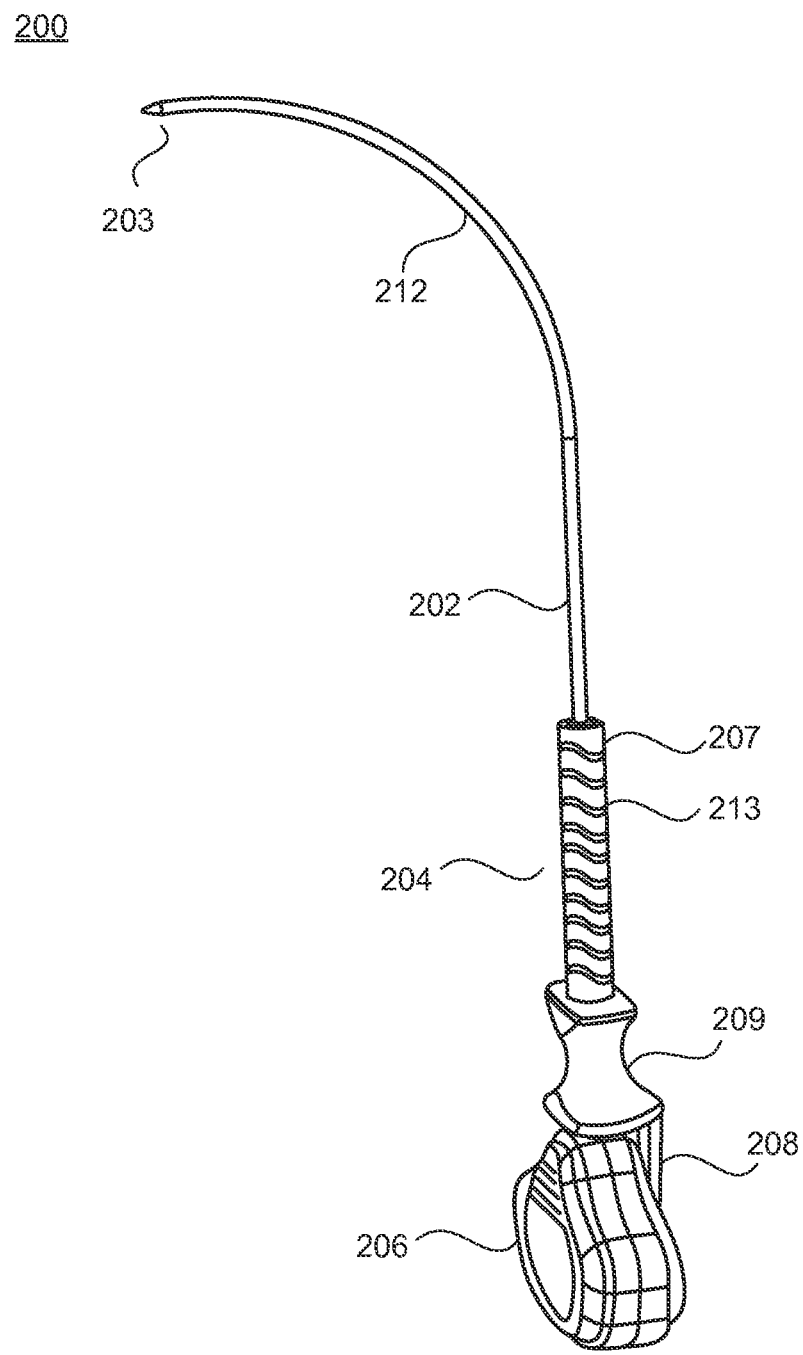
FIG. 2C illustrates the pusher member assembled with the needle member and coupled to the handle.

FIGS. 2A-2C illustrate components of a re-usable medical device 200 having a pusher member 204 with a plurality of recesses 213 disposed on a sheath 207 of the pusher member 204 according to various aspects. For example, the pusher member 204 may have a bendable portion that is configured to conform to the shape of a needle member 202 due to the plurality of recesses 213. FIG. 2A illustrates a perspective of the pusher member 204 that is configured to slide onto the needle member 202 according to an aspect. FIG. 2B illustrates the bendable portion of the pusher member 204 conforming to the shape of the needle member 202 when placed over the needle member 202 according to an aspect. FIG. 2C illustrates the pusher member 204 assembled with the needle member 202 and coupled to the handle 206 according to an aspect.

Referring to FIGS. 2A-2C, the medical device 200 may include the handle 206, the needle member 202, and the pusher member 204 having an extension member 208, a handle portion 209, and the sheath 207. The needle member 202 may include a distal end portion 203 and a proximal end portion 210. The proximal end portion 210 of the needle member 202 may be coupled to the handle 206. Also, the needle member 202 may include a curved portion 212.

The sheath 207, the handle portion 209, and the extension member 208 may be formed of a unitary plastic-based component. However, the sheath 207 of the pusher member 204 may include the plurality of recesses 213 along a length (or a portion thereof) of the sheath 207 such that the sheath 207 can bend to the curvature of the curved portion 212 of the needle member 202. The recesses 213 are defined on the outer surface of the sheath 207. In some examples, each of the recesses 213 may be relatively linear. In other examples, each of the recesses 213 may have a curved shaped. In some examples, the recesses 213 may wrap around the outer surface of the sheath 207 (e.g., circle around the sheath 207). In other examples, the recesses 213 may wrap around a portion of the outer surface of the sheath 207 (e.g., c-shaped, u-shaped, etc.). The recesses 213 may be considered slots, openings, grooves, or cut-out portions that are distributed along the length of the sheath 207. In some examples, the recesses 213 may be equally spaced apart from one another along the length of the sheath 207. In some examples, the recesses 213 may be generally perpendicular to a central axis of the sheath 207.

As shown in FIG. 2A, when assembling the medical device 200, the pusher member 204 may slide onto the needle member 202 (via the lumen of the pusher member 204) in the proximal direction. Referring to FIG. 2B, the bendable sheath 207 may be configured to conform to the shape of the curved portion 212 of the needle member 202 as the pusher member 204 continues to be moved towards the handle 206 due to the recesses 213. Also, although the handle portion 209 of the pusher member 204 is relatively rigid (or less flexible than the sheath 207), since the handle portion 209 is relatively short, the handle portion 209 may easily slide over the curved portion 212 of the needle member 202. Referring to FIG. 2C, the pusher member 204 slides over the needle member 202 towards the handle 206, and is then coupled to the handle 206. As shown in FIG. 2C, the bendable pusher member 204 bends back into a relatively linear configuration since the portions of the needle member 202 proximate to the handle 206 are relatively linear. The details on how the extension member 208 of the pusher member 204 is coupled to the handle 206 are further described with reference to FIGS. 5A-5C.

Figure 3A:
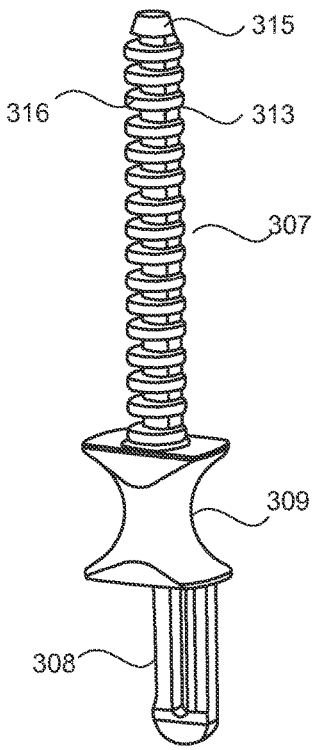
FIG. 3A illustrates a perspective of a pusher member.
Figure 3B:
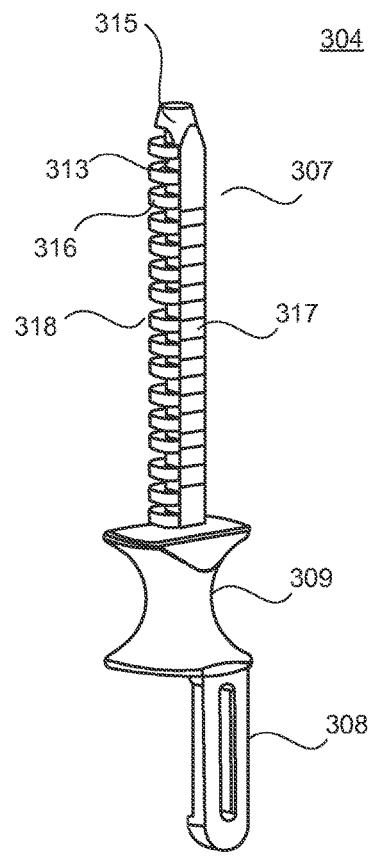
FIG. 3B illustrates another perspective of the pusher member.

FIGS. 3A-3B illustrate a pusher member 304 according to various aspects. In some examples, the pusher member 304 may be the pusher member 204 of FIGS. 2A-2C or the pusher member 104 of FIGS. 1A-1B. The pusher member 304 may include a sheath 307, a handle portion 309, and an extension member 308. FIG. 3A illustrates the pusher member 304 according to a first angle. FIG. 3B illustrates the pusher member 304 according to a second angle. Referring to FIGS. 3A-3B, the sheath 307 of the pusher member 304 may be D-shaped. For example, the sheath 307 may include a rounded outer surface 318 and a flat surface 317. The rounded outer surface 318 and the flat surface 317 may define an internal lumen. The rounded outer surface 318 may extend around a portion of the outer surface (e.g., c-shaped). The flat surface 317 may extend to the edges of the rounded outer surface 318. In some examples, the flat surface 317 may have a relatively smooth surface. In some examples, the flat surface 317 may be a silicone member that provides a flat, flexible, and/or stretchable surface for the user to guide the pusher member 304. Also, the sheath 307 may include a tapered portion 315 at the distal end of the sheath 307. The tapered portion 315 may taper in the distal direction of the pusher member 304.

The rounded outer surface 318 may define a plurality of recesses 313 disposed along the length of the sheath 307. The recesses 313 may be openings, grooves, or cut-out portions of the sheath 307 that extend towards the lumen of the sheath 207 (but not through the lumen of the sheath 307). The recesses 313 may include any number of recesses such as any number greater or equal to two. In some examples, the recesses 313 may be considered to define a plurality of disc portions 316 where each disc portion 316 is defined by two adjacent recesses 313. The disc portions 316 may have a shape that corresponds to the shape of the rounded outer surface 318. In some examples, the disc portions 316 may have a semi-circular shape. The diameter of the sheath 307 at the disc portions 316 may be greater than the diameter of the sheath 307 at the recesses 313. The disc portions 316 and the recesses 313 may alternate from the proximal end of the sheath 307 to the distal end of the sheath 307. In some examples, the recesses 313 and/or the disc portions 316 may be equally spaced apart from each other along the length of the sheath 307.

Figure 4:
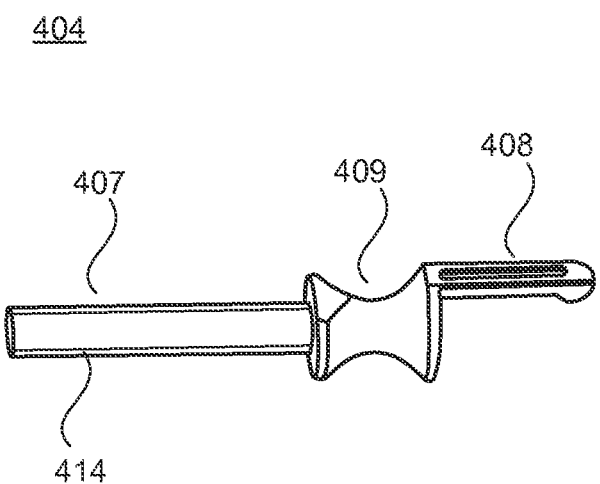
FIG. 4 illustrates a pusher member.

FIG. 4 illustrates a pusher member 404 according to another aspect. For example, the pusher member 404 may include a sheath 407, a handle portion 409, and an extension member 408, which have been described with reference to the previous figures. However, in the example of FIG. 4, the sheath 407 may be a flexible tube 414. The flexible tube 414 may be configured to conform to the shape of the needle. The flexible tube 414 may be a tubular structure having an inner diameter and an outer diameter. The inner diameter may define the lumen of the sheath 407. The flexible tube 414 may be formed from any type of flexible material including any type of plastic-based materials. In some examples, the flexible tube 414 may be a polyethylene material. In some examples, the handle portion 409 and the extension member 408 may be a unitary plastic-based component, and the flexible tube 414 may be coupled to the handle portion 409.

For assembling the re-usable medical device, the pusher member 404 may slide onto a needle member (e.g., the needle member 102/202/302) in the proximal direction such that the flexible tube 414 conforms to the curved or bent shape of the needle member in the same manner discussed with reference to the previous figures. For disassembling the medical device, the pusher member 404 may slide in the distal direction such that the flexible tube 414 conforms to the curved or bent shape of the needle member in the same manner discussed with reference to the previous figures.

Figure 5A:
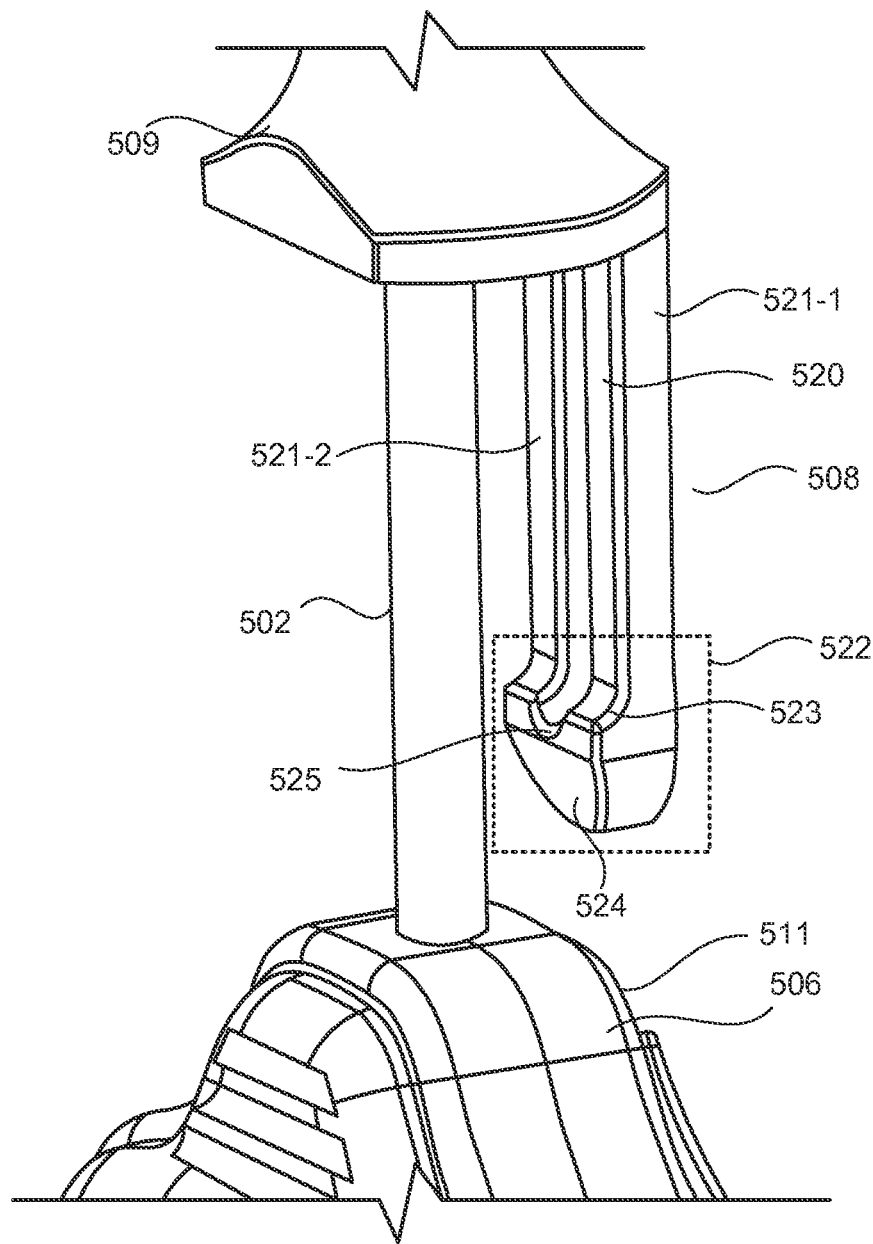
FIG. 5A illustrates a perspective of an extension member and a track of a handle in a configuration where the extension member is decoupled from the handle.
Figure 5B:
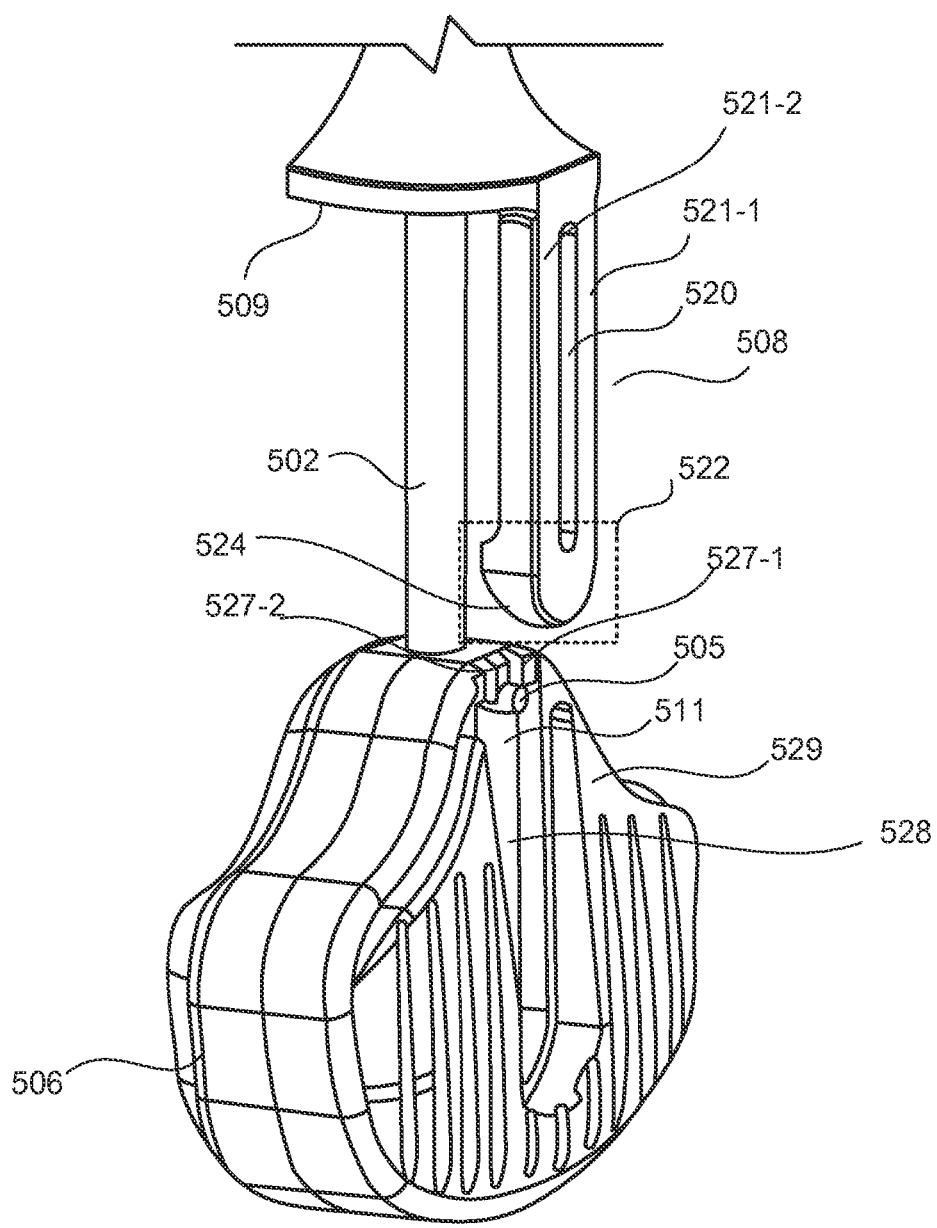
FIG. 5B illustrates another perspective of the extension member and the track of the handle in the configuration where the extension member is decoupled from the handle.
Figure 5C:
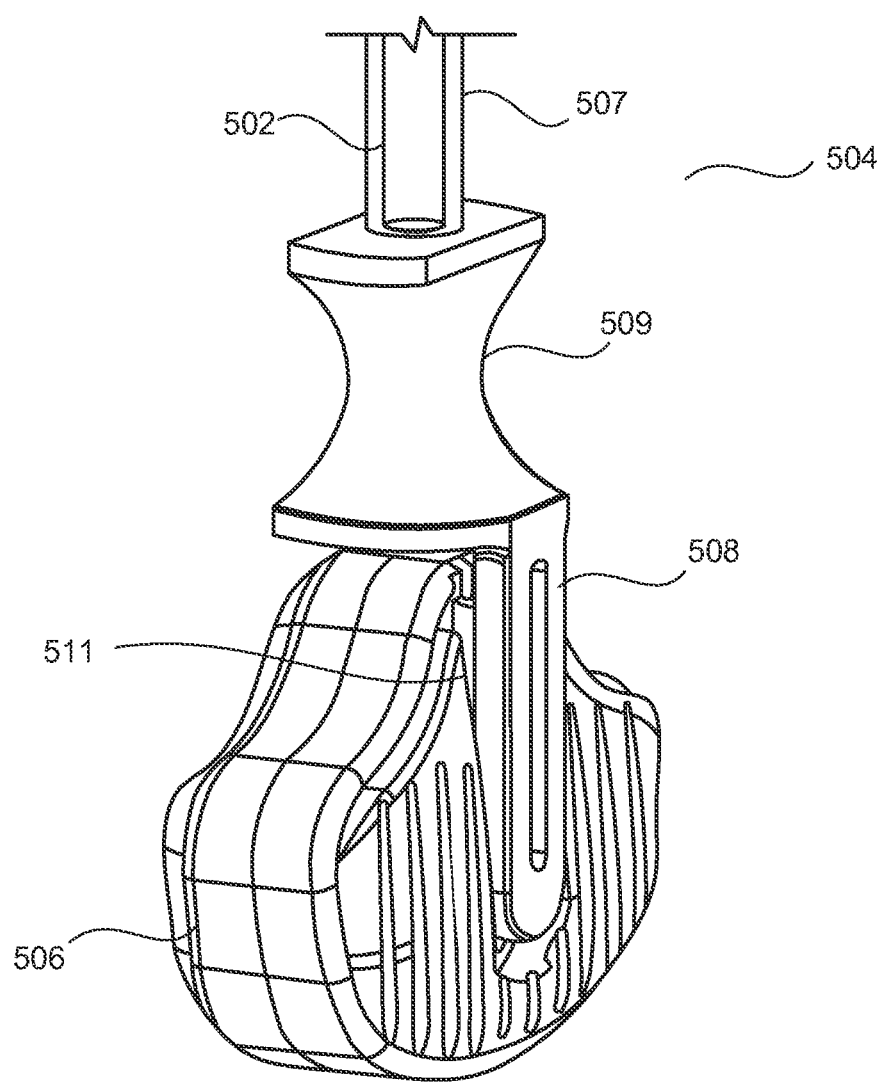
FIG. 5C illustrates the extension member of the pusher member coupled to the handle such that the extension member can slide within the track of the handle.

FIGS. 5A-5C illustrate a pusher member 504 and a handle 506 according to various aspects. The pusher member 504 may include a sheath 507, a handle portion 509, and an extension member 508. The sheath 507 may be the sheath 307 of FIG. 3 or the sheath 407 of FIG. 4. FIGS. 5A-5C illustrate the details of how the pusher member 504 is coupled to the handle 506 which may be extended to any of the implementations discussed herein. FIG. 5A illustrates a perspective of the extension member 508 and a track 511 of the handle 506 in a configuration where the extension member 508 is decoupled from the handle 506 according to an aspect. FIG. 5B illustrates another perspective of the extension member 508 and the track 511 of the handle 506 in the configuration where the extension member 508 is decoupled from the handle 506 according to an aspect. FIG. 5C illustrates the extension member 508 of the pusher member 504 coupled to the handle 506 such that the extension member 508 can slide within the track 511 of the handle 506 according to an aspect.

Referring to FIGS. 5A-5C, the extension member 508 may be coupled to a proximal end portion of the handle portion 509. The extension member 508 may be coupled to a top surface on the proximal end portion of the handle portion 509. The extension member 508 may proximally extend in a direction parallel to a central axis of the needle member 502. Referring to FIGS. 5A-5B, the extension member 508 may define a slot 520. For example, the extension member 508 may define the slot 520 through a middle portion of the extension member 508. Referring to FIG. 5B, a protrusion component 505 of the handle 506 may be configured to slide within the slot 520. The extension member 508 may include a first leg 521-1 and a second leg 521-2 that is spaced apart from the first leg 521-1. The space between the first leg 521-1 and the second leg 521-2 may define the slot 520.

The extension member 508 may include an enlarged portion 522 at the proximal end portion of the extension member 508. When the pusher member 504 is moved to its extended position, the enlarged portion 522 may engage the protrusion component 505 on the handle 506 to prevent further distal movement during the surgical procedure. The enlarged portion 522 may join the first leg 521-1 and the second leg 521-2 defining one end of the slot 520. For example, the enlarged portion 522 may include a joining portion 525 that connects the first leg 521-1 and the second leg 521-2, thereby closing the slot 520. The enlarged portion 522 may include a concave portion 523 at each end of the first and second legs 521 that transitions to a larger thickness of the enlarged portion 522. At the proximal end of the extension member 508, the enlarged portion 522 may include a tapered portion 524. For instance, the tapered portion 524 may permit the extension member 508 to mate with the handle 506 and slide into the track 511. In some examples, the enlarged portion 522 may be considered a lip that perpendicularly extends from the surface of the extension member 508.

The extension member 508 may be flexible. For example, when coupling the extension member 508 to the track 111 of the handle 506, the extension member 508 (e.g., in particular, the enlarged portion 522) may flex to slide over the protrusion component 505 and then flex back into its original linear configuration (thereby mate with the track 511) once the enlarged portion 522 is moved past the protrusion component 505. Furthermore, the tapered portion 524 of the enlarged portion 522 may facilitate the transition over the protrusion component 505.

Referring to FIGS. 5A-5B, the track 511 may include a recess 528. In some examples, the recess 528 may have a shape that corresponds to the extension member 508 of the pusher member 504 such that the extension member 508 can fit and slide within the recess 528. In some examples, the recess 528 may have a u-shape structure such that lateral edges that define the u-shaped recess are disposed parallel with the longitudinal axis of the handle 506, and the rounded portion of the u-shaped recess intersects with the longitudinal axis of the handle 506. Portions of the recess 528 extend on both sides the longitudinal axis of the handle 506. The recess 528 may extend below a top surface 529 of the handle 506. The recess 528 may have a length extending from the start of the recess (e.g., the distal end of the handle 506) to the end of the recess (e.g., the proximal end portion of the handle 506).

As indicated above, the protrusion component 505 may be configured to prevent the pusher member 504 from being de-coupled from the handle 506 during the surgical procedure. The protrusion component 505 may be an example of the protrusion component 105 of FIGS. 1A-1C. The protrusion component 505 may be coupled to a lowered surface defined by the recess 528 (e.g., from the top surface 529 of the handle portion 509), and may extend into the recess 528 in a direction perpendicular to the length of the recess 528. In some examples, the protrusion component 505 may have a circular shape. In other examples, the protrusion component 505 may have a non-circular shape. In some examples, the protrusion component 505 may be a boss. In addition, in some examples, the handle 506 may define a first ramp member 527-1 and a second ramp member 527-2 that are disposed proximate to each side of the protrusion component 505. The ramp members 527 may ramp towards the protrusion component 505 in order to facilitate the transition over the protrusion component 505.

When the pusher member 504 moves the retracted position to the extended position, the protrusion component 505 slides within the recess 528 and the slot 520 defined by the extension member 508. Then, in the extended position, the enlarged portion 522 engages with the protrusion component 505 to prevent further distal movement of the pusher member 504 during the surgical procedure. However, when de-coupling the pusher member 504 from the handle 506, additional distal force may be applied to the pusher member 504 such that the extension member 508 flexes to permit the enlarged portion 522 to slide over the protrusion component 505.

Figure 6A:
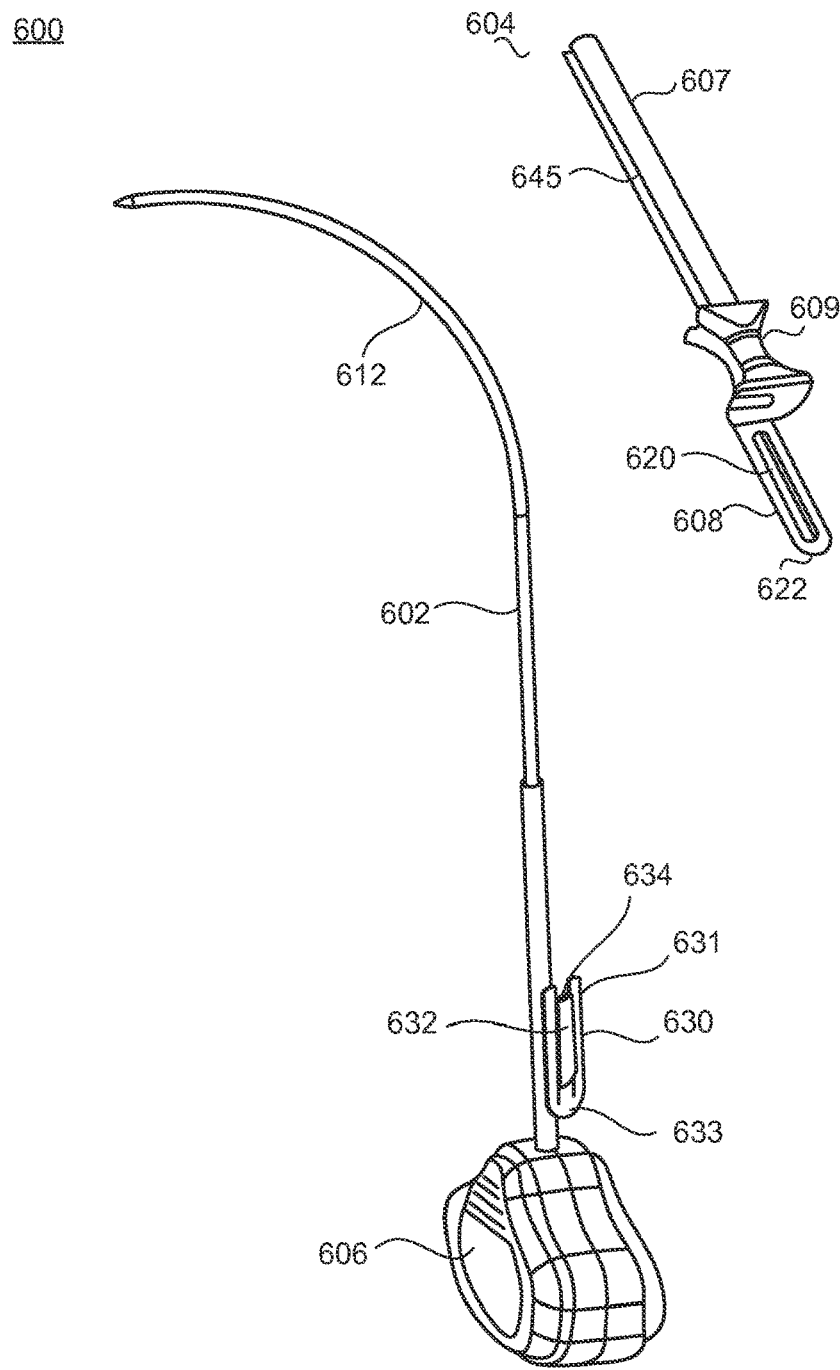
FIG. 6A illustrates disassembled components of a medical device.
Figure 6B:
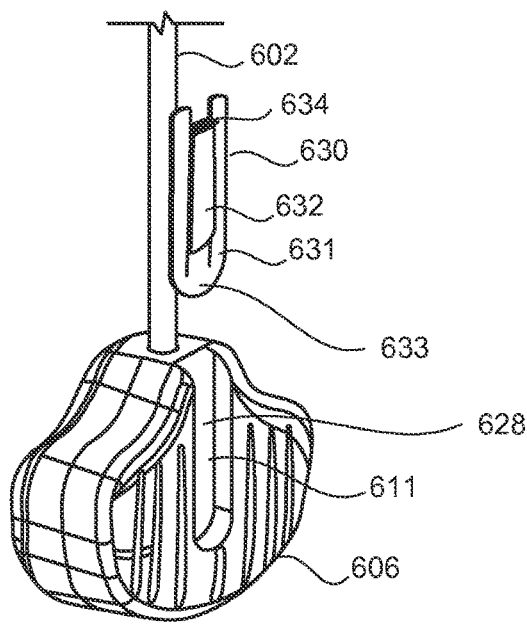
FIG. 6B illustrates an insert decoupled from a handle.
Figure 6C:
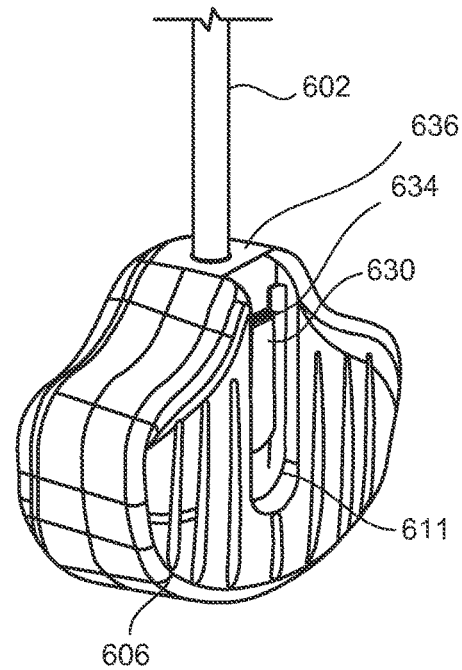
FIG. 6C illustrates the insert coupled to the handle.
Figure 6D:
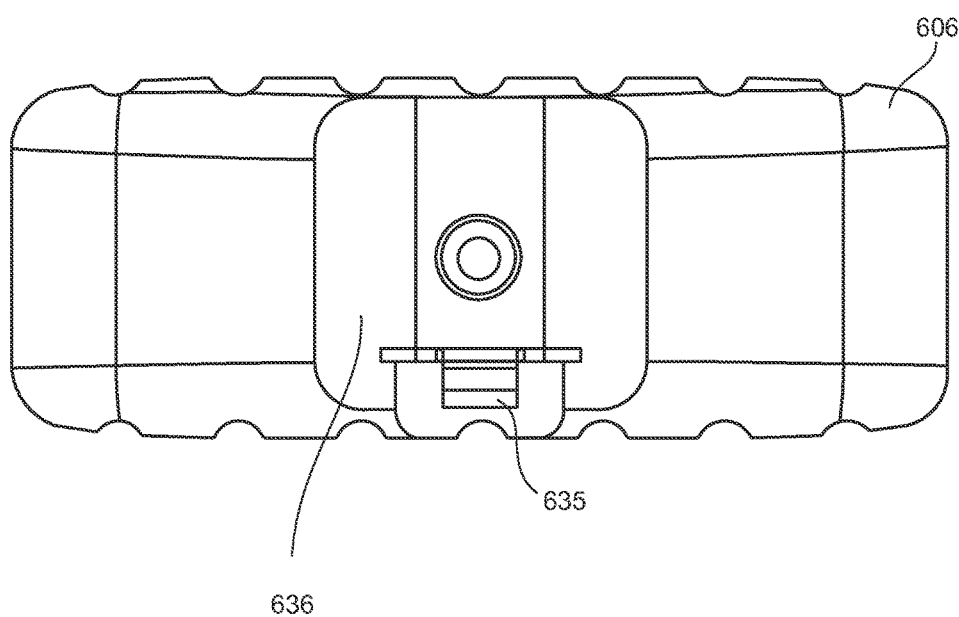
FIG. 6D illustrates a side view of the handle depicting a slot.
Figure 6E:
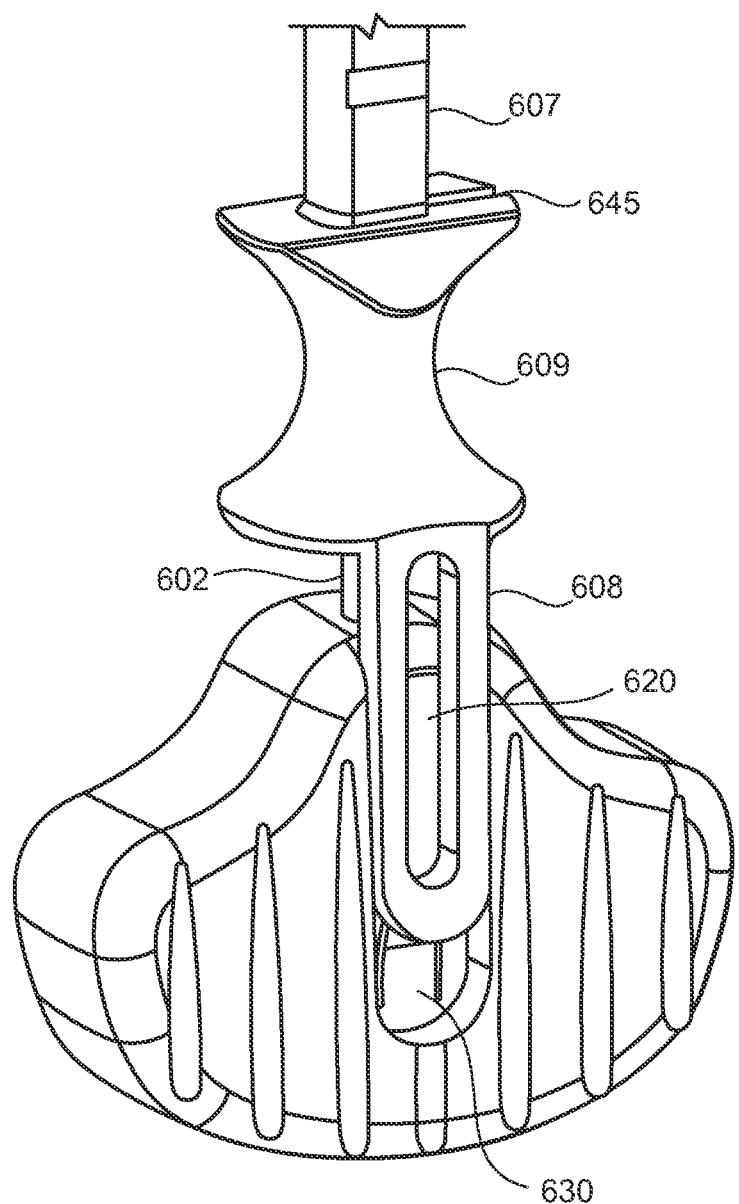
FIG. 6E illustrates the insert coupled to the handle and a pusher member coupled to the handle via the insert.

FIGS. 6A-6E illustrate a medical device 600 having a pusher member 604, a needle member 602, a handle 606, and an insert 630 configured to be inserted into the handle 606 in order to couple the pusher member 604 to the handle 606 according to various aspects. The insert 630 may be an example of the protrusion component 105 of FIGS. 1A-1C. FIG. 6A illustrates the disassembled components of the medical device 600 according to an aspect. FIG. 6B illustrates the insert 630 decoupled from the handle 606 according to an aspect. FIG. 6C illustrates the insert 630 coupled to the handle 606 according to an aspect. FIG. 6D illustrates a side view of the handle 606 depicting a slot 635 according to an aspect. FIG. 6E illustrates the insert 630 coupled to the handle 606 and the pusher member 604 coupled to the handle 606 via the insert 630 according to an aspect.

The pusher member 604 may include a sheath 607, a handle portion 609, and an extension member 608. The extension member 608 may be the extension member 508 described with reference to FIGS. 5A-5C. For example, the extension member 608 may define a slot 620 and an enlarged portion 622. Also, the pusher member 604 may define a slot 645. For example, the slot 645 may extend through or along the length of the handle portion 609 and the sheath 607. As such, the structure of the pusher member 604 defining the lumen and the slot 645 may be substantially c-shaped or u-shaped. The pusher member 604 may be de-coupled from the needle member 602 via the slot 645. In other examples, the pusher member 604 does not define the slot 645. Rather, the pusher member 604 may be a bendable pusher member, e.g., any of the pusher members described with reference to FIGS. 2-4.

Referring to FIGS. 6A-6E, the insert 630 may include a base 631 and a flexible projection 632. The flexible projection 632 may extend from a surface of the base 631, and is bendable towards (and away) from the surface of the base 631. In this example, referring to FIG. 6D, the handle 606 may define a slot 635 on the front surface 636 of the handle 606. In some examples, the slot 635 may be T-shaped. However, the slot 635 may include other types of dimensions that generally correspond to the shape of the insert 630. Referring to FIGS. 6B-6E, when assembling the medical device 600, the base 631 of the insert 630 is inserted into the slot 635 of the handle 606 in the proximal direction. In some examples, the insert 630 is permanently fixed to the handle 606 such that the insert 630 is not removable after the insert 630 is inserted into the slot 635 of the handle 606. In other examples, the insert 630 is not permanently fixed to the handle 606 where the fit of the insert 630 to the slot 635 of the handle 606 is designed such that the insert 630 remains in position within the slot 635 of the handle 606 during the surgical procedure, but with more substantial force, the insert 630 may be removed from the slot 635 of the handle 606 after the surgical procedure to be subsequently cleaned and later re-inserted back into the handle 606 for the next surgical procedure.

Referring to FIGS. 6B-6C, when inserted through the slot 635 of the handle 606, the flexible projection 632 of the insert 630 springs outwardly from the base 631 into the recess 628 of the track 611. Further, the flexible projection 632 of the insert 630 may include a protrusion portion 634 on its distal end that engages with an enlarged portion 622 of the extension member 608 to limit the travel distance of the pusher member 604 when the pusher member 604 moves to its extended position. For example, the flexible projection 632 may slide within the slot 620 of the extension member 608 during movement within the track 611 until the enlarged portion 622 of the extension member 608 engages with the protrusion portion 634 of the flexible projection 632. Also, the flexible projection 632 of the insert 630 may include a rounded portion 633 at its proximal end that corresponds to a shape of the back end of the track 611.

In some examples, the base 631 and the flexible projection 632 may be a molded or stamped sheet metal component. In some examples, the flexible projection 632 may be considered a tongue that is sprung outwardly. After the medical procedure, when disassembling the medical device 600, the pusher member 604 may be moved to its extended position. Then, the flexible projection 632 may be depressed inwardly towards the base 631 by a user so that the extension member 608 can slide past the protrusion portion 634 of the flexible projection 632, thereby decoupling the pusher member 604 from the handle 606. Next, the pusher member 604 can be removed from the needle member 602 and cleaned separately from the other components of the medical device 600 so that the hard-to-reach areas (e.g., the lumen of the pusher member 604) can be easily accessed for effective cleaning and sterilization in preparation for a subsequent surgical procedure. For example, if the pusher member 604 includes the slot 645, the pusher member 604 may be removed from the needle member 602 via the slot. However, if the pusher member 604 does not define the slot 645 but rather is implemented as the bendable pusher member described in FIGS. 2-4, the pusher member 604 may be removed over the distal end of the needle member 602.

Figure 7:
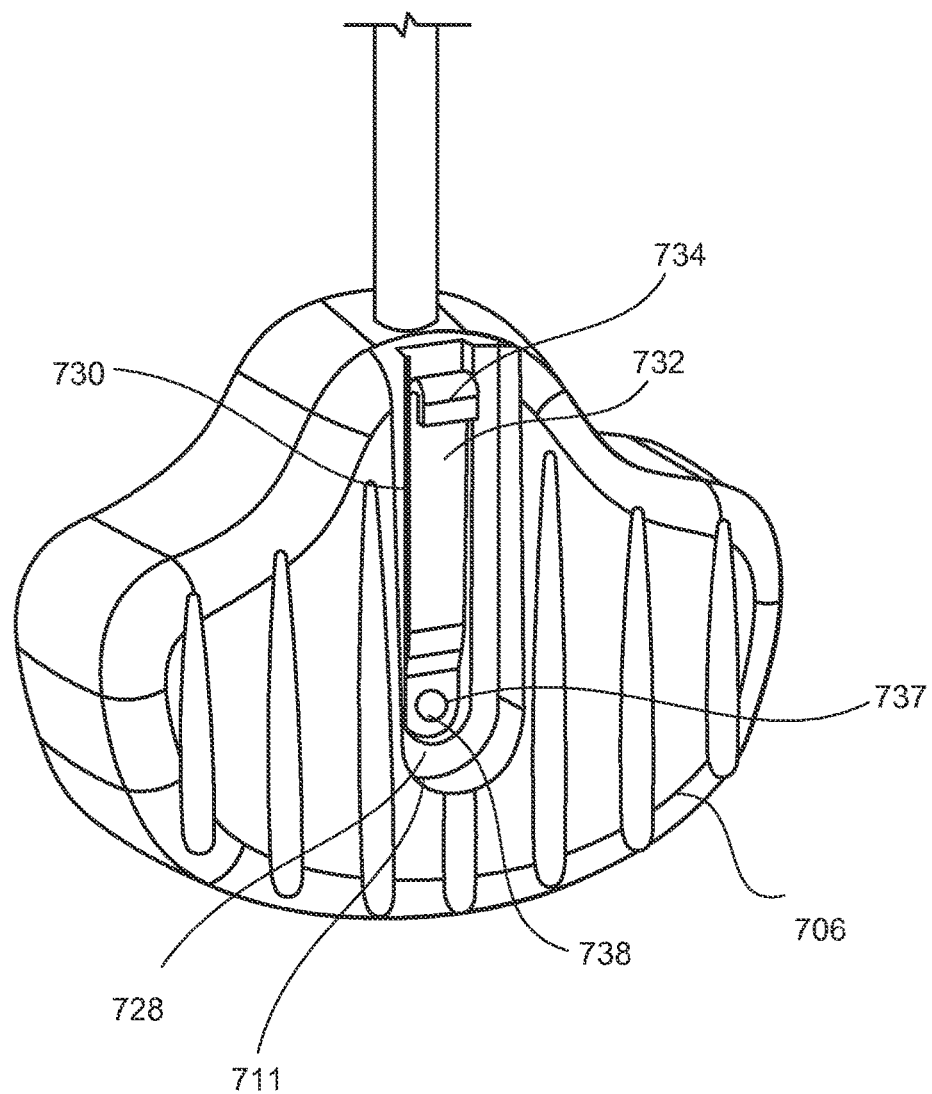
FIG. 7 illustrates an insert coupled to a handle.

FIG. 7 illustrates an insert 730 coupled to a handle 706 according to another aspect. For example, the insert 730 may be a variation of the insert 630 of FIGS. 6A-6E. In the example of FIG. 7, the insert 730 includes a flexible projection 732. The flexible projection 732 may include a projection member 734 that extends from a surface of the flexible projection 732. In some examples, the projection member 734 may be a portion of the flexible projection 732 that curves outwardly from its surface. Also, in contrast to the insert 630 of FIGS. 6A-6E, the insert 730 does not include the base 631. Furthermore, the handle 706 does not define a slot, but rather the flexible projection 732 is coupled within the recess 728 of the track 711. For example, the flexible projection 732 may be coupled to the handle 706 within the recess 728 of the track 711. In some examples, the flexible projection 732 may be coupled within the recess 728 of the track 111 using a hole and boss coupling mechanism. For example, the flexible projection 732 may define a hole 738, and a boss 737 is coupled to the lowered surface of the recess of the track 711 and extends outwardly from the lowered surface of the recess 728. The fit between the hole 738 and the boss 737 may be designed to create a permanent assembly or semi-permanent assembly such that the flexible projection 732 remains coupled to the handle 706 during the surgical procedure, but may be disassembled by the user with more substantial force.

Figure 8A:
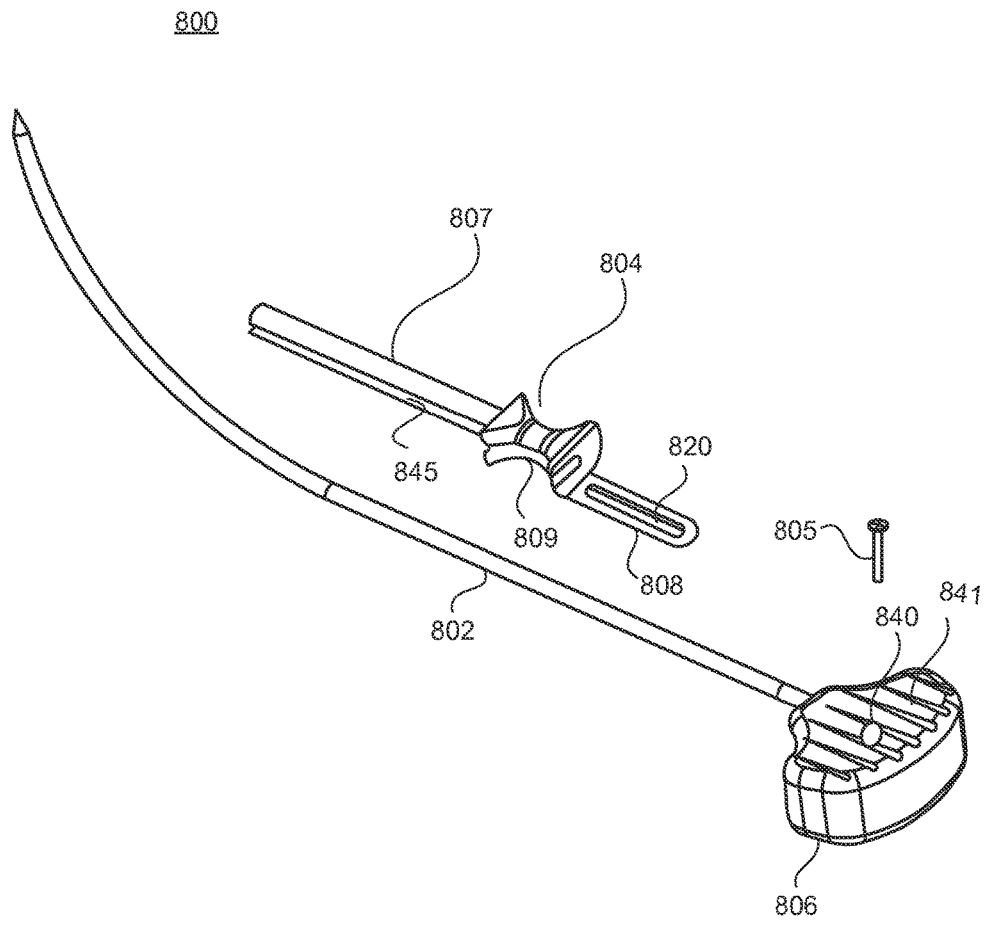
FIG. 8A illustrates disassembled components of a medical device.
Figure 8B:
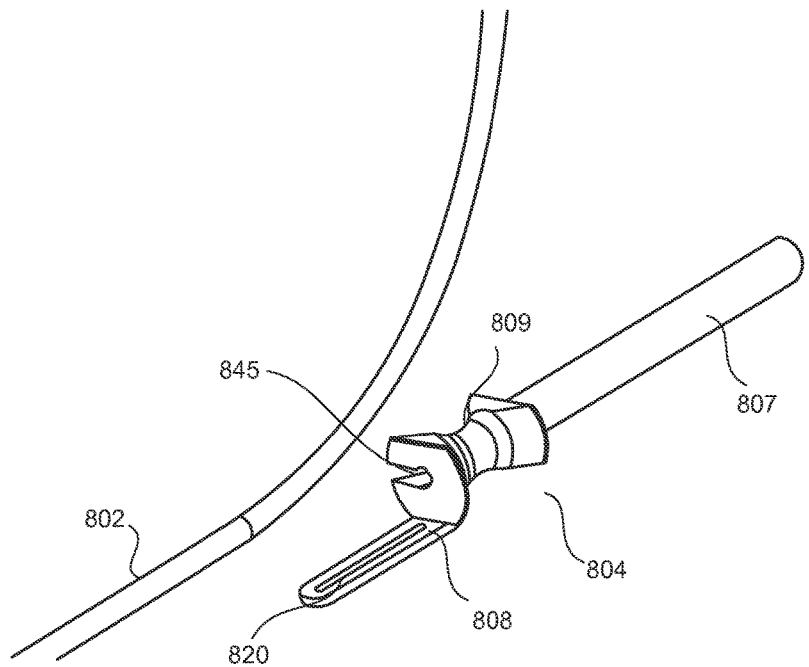
FIG. 8B illustrates a perspective of a pusher member and a needle member.
Figure 8C:
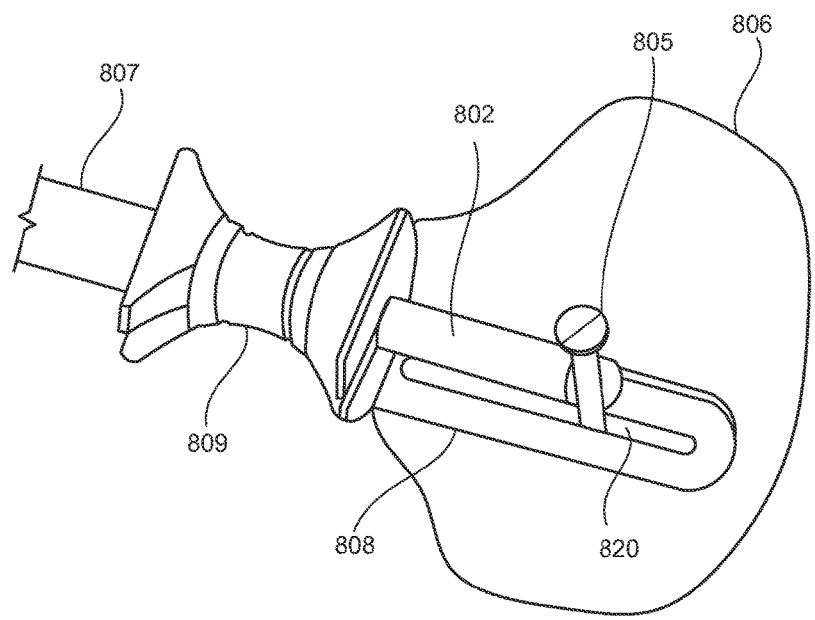
FIG. 8C illustrates a perspective of a removable pin within a slot defined by an extension member.
Figure 8D:
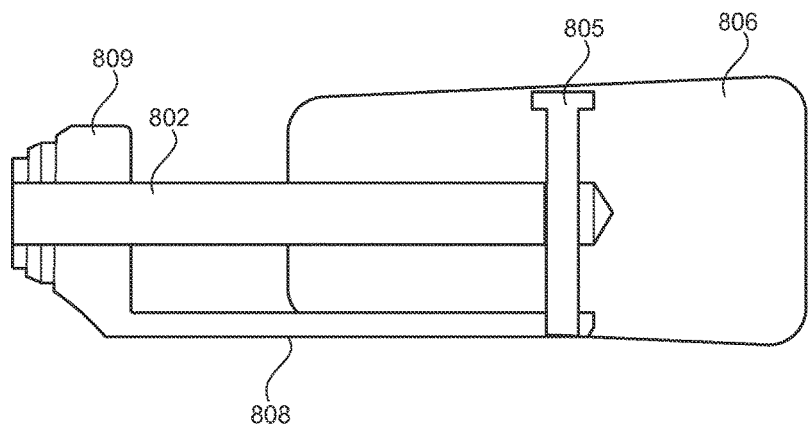
FIG. 8D illustrates a side view of a portion of the medical device 800 depicting the removable pin.
Figure 8E:
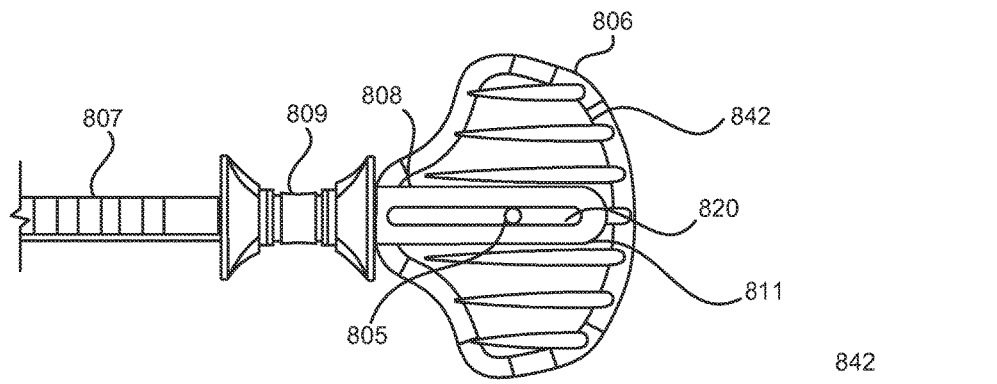
FIG. 8E illustrates a top view of a portion of the medical device depicting the pusher member within the retracted position.

FIGS. 8A-8F illustrate various perspectives of a medical device 800 that includes a removable pin 805 configured to prevent distal movement of the pusher member 804 according to various aspects. FIG. 8A illustrates disassembled components of the medical device 800 including a pusher member 804 having a sheath 807, a handle portion 809, and an extension member 808, a needle member 802 coupled to a handle 806, and the removable pin 805. FIG. 8B illustrates a perspective of the pusher member 804 and the needle member 802. In some examples, the pusher member 804 may be removable from the needle member 802 via a slot defined by the pusher member 804. FIG. 8C illustrates a perspective of the removable pin 805 within a slot 820 defined by the extension member 808. FIG. 8D illustrates a side view of a portion of the medical device 800 depicting the removable pin 805 limiting the distal movement of the pusher member 804. FIG. 8E illustrates a top view of a portion of the medical device 800 depicting the pusher member 804 within the retracted position where a portion of the removable pin 805 is disposed within the track 811 of the handle 806 and the slot 820 of the extension member 806.

Figure 8F:
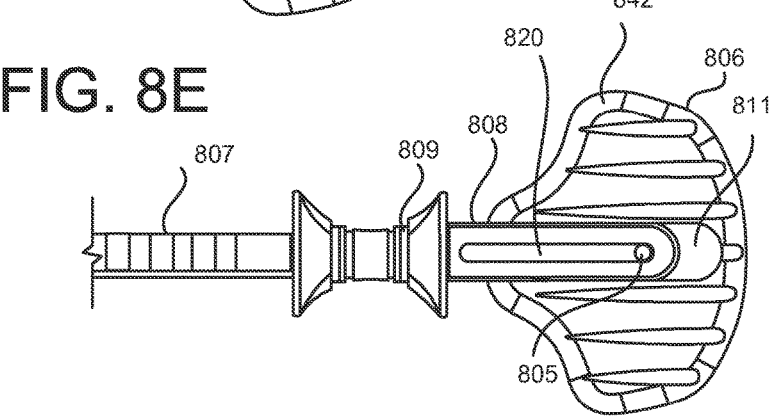
FIG. 8F illustrates a top view of a portion of the medical device depicting the pusher member within the extended position.

FIG. 8F illustrates a top view of a portion of the medical device 800 depicting the pusher member 804 within the extended position where the portion of the removable pin 805 engages the extension member 808 at the end of the slot 820 thereby limiting distal movement of the pusher member 804.

The removable pin 805 may be an example of the protrusion component 105 of FIGS. 1A-1C. In some examples, the extension member 808 does not include the enlarged portion (e.g., the enlarged portion 522 of FIG. 5B) discussed with reference to some of the other implementations. Referring to FIGS. 8A-8F, in some examples, the pusher member 804 may define the slot 845 that permits the pusher member 804 to be decoupled from the needle member 802 from its side. For example, the sheath 807 and the handle portion 809 may define the slot 845. However, in other examples, the pusher member 804 does not define the slot 845, but rather is implemented as the bendable pusher member as described in FIGS. 2-4. The handle 806 may define the through-hole 840 configured to receive the pin 805. The through-hole 840 may extend from the surface 841 of the handle 806 to the surface 842 of the handle.

When assembling the medical device 800, the pusher member 804 may be coupled to the needle member 802 and moved towards the proximal end portion of the needle member 802. Then, the extension member 808 may be coupled to the track 811, e.g., disposed within the recess of the track 811. The pin 805 is inserted into the through-hole 840. For example, the pin 805 may extend through the handle 106 such that a portion of the pin 805 extends into the recess of track 811, and this portion of the pin 805 that protrudes into the recess of the track 811 limits the travel distance of the pusher member 804 and prevents it from being disassembled. In some examples, the pin 805 may include a threaded screw, and the through-hole of the handle 806 includes grooves configured to engage with the threaded screw. For re-use of the medical device 600, the pin 805 may be removed (e.g., unscrewed) and the pusher member 804 may be coupled from the handle 106, and then decoupled from the needle member 802.

FIGS. 9A-9E illustrate various perspectives of a medical device 900 that includes an adjustable pin assembly 905 configured to prevent distal movement of the pusher member 904 according to various aspects. The features described in FIGS. 9A-9B may be implemented in any of the medical devices described herein. The adjustable pin assembly 905 may be an example of the protrusion component 105 of FIGS. 1A-1C. The medical device 900 may include a pusher member 904, a handle 906, a needle member 902 coupled to the handle 906, and the adjustable pin assembly 905. The pusher member 904 may include a sheath 907, a handle portion 909, and an extension member 908. The extension member 908 may define a slot 920.

Figure 9A:
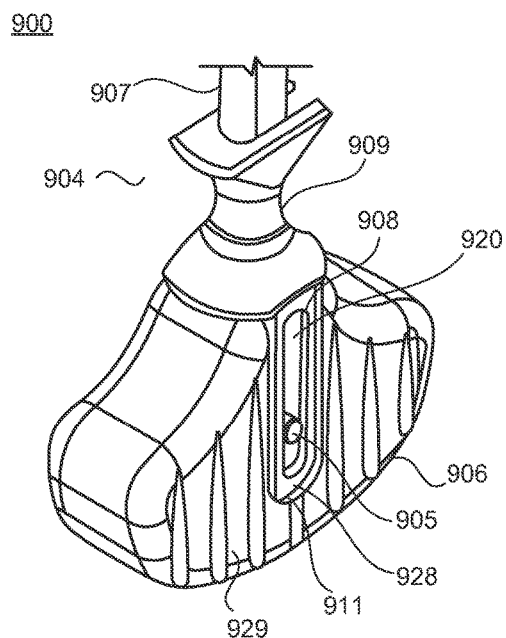
FIG. 9A illustrates a perspective of a pusher member coupled to a handle with an adjustable pin assembly in a first configuration.
Figure 9B:
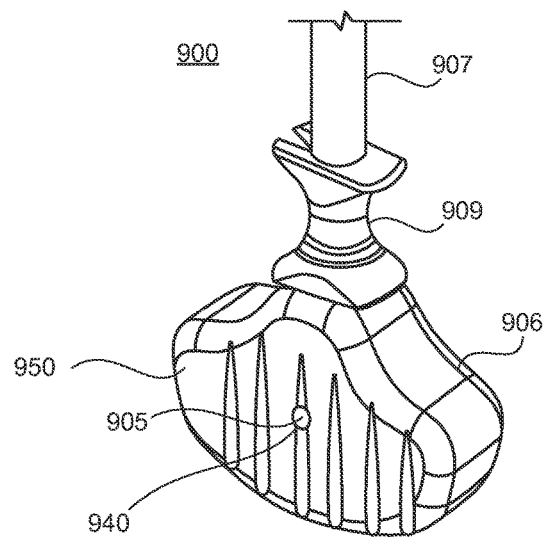
FIG. 9B illustrates another perspective of the pusher member coupled to the handle with the adjustable pin assembly in the first configuration.
Figure 9C:
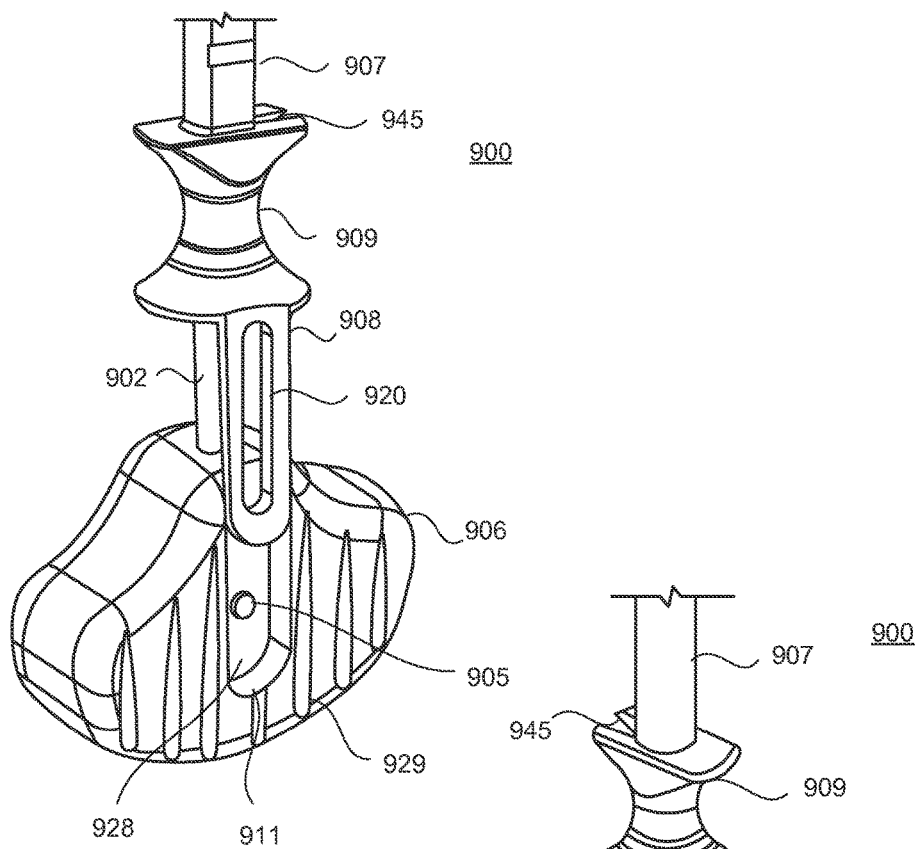
FIG. 9C illustrates a perspective of the pusher member and the handle with the adjustable pin assembly in a second configuration.
Figure 9D:
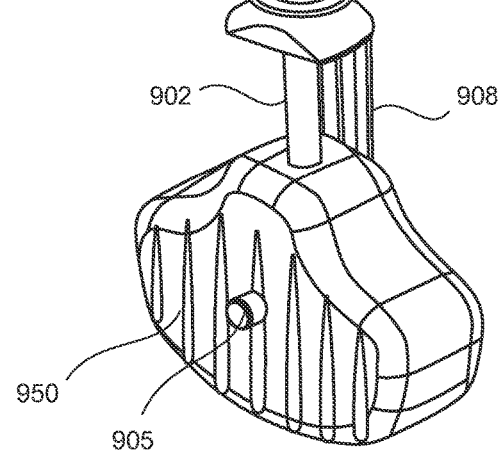
FIG. 9D illustrates another perspective of the pusher member and the handle with the adjustable pin assembly in the second configuration.

FIG. 9A illustrates a perspective of the pusher member 904 coupled to the handle 906 with the adjustable pin assembly 905 in a first configuration according to an aspect. FIG. 9B illustrates another perspective of the pusher member 904 coupled to the handle 906 with the adjustable pin assembly 905 in the first configuration. For example, the adjustable pin assembly 905 is configured in the first configuration when the medical device 900 is used during the surgical procedure. FIG. 9C illustrates a perspective of the pusher member 904 and the handle 906 with the adjustable pin assembly 905 in a second configuration. FIG. 9D illustrates another perspective of the pusher member 904 and the handle 906 with the adjustable pin assembly 905 in the second configuration. The adjustable pin assembly 905 may be manipulated to the second configuration for disassembling the medical device 900.

As shown in FIGS. 9A-9B, the handle 906 may define a through-hole 940 that extends from the surface within the recess 928 of the track 911 to the bottom surface 950 of the handle 906. For example, one opening of the through-hole 940 is disposed within the recess 928, and the other opening of the through-hole 940 is disposed on the bottom surface 950. The through-hole 940 may linearly extend between the openings. The adjustable pin assembly 905 may be disposed within the through-hole 940. In some examples, the adjustable pin assembly 905 may include an elongated tubular structure having a length that is greater than the length of the through-hole 940. The elongated tubular structure of the adjustable pin assembly 905 may have a diameter slightly less than the diameter of the through-hole 940 so that the adjustable pin assembly 905 may slide through the through-hole 940. Also, because the length of the adjustable pin assembly 905 is larger than the length of the through-hole 940, a portion of the adjustable pin assembly 905 may extend out of one (or both) of the openings of the through-hole 940.

As shown in FIG. 9A, in the first configuration, a portion of the adjustable pin assembly 905 extends into the recess 928 of the track 911. As shown in FIG. 9B, in the first configuration, the other end of the adjustable pin assembly 905 is relatively flush with the bottom surface 950 of the handle 906. During the surgical procedure, the pusher member 904 may be distally moved such that the portion of the adjustable pin assembly 905 slides within the slot 920 of the extension member 908 until reaching the back end of the slot 920. The movement of the pusher member 904 may be stopped by the adjustable pin assembly 905 engaging with the portion of the extension member 908 defined by the back end the slot 920. The adjustable pin assembly 905 may remain in the first configuration during the course of the surgical procedure.

After the surgical procedure, in order to decouple the pusher member 904 from the handle 906, a user may press the portion of the adjustable pin assembly 905 that extends into the recess 926 such that the adjustable pin assembly 905 is moved to the second configuration. FIGS. 9C and 9D depict the adjustable pin assembly 905 in the second configuration. As shown in FIG. 9C, the adjustable pin assembly 905 is relatively flush with the lowered surface of the recess 928. As shown in FIG. 9D, a portion of the adjustable pin assembly 905 extends from the bottom surface 950 of the handle 906. As a result, because there are no protrusions extending into the recess 926, the extension member 908 can slide off the track 911 of the handle 906. Then, the pusher member 904 can be decoupled the needle member 902 (e.g., via the slot 945 or if the pusher member 904 is implemented as the bendable pusher member of FIGS. 2-4 by sliding the pusher member 904 over the distal end of the needle member), and the components of the medical device 900 can be sterilized, and then re-assembled.

For re-assembling the medical device 900, the adjustable pin assembly 905 is placed in the second configuration, the pusher member 904 is inserted onto the needle member 902 (e.g., via the slot 945 or by sliding over the distal end portion of the bendable needle member), the extension member 908 of the pusher member 904 is moved into the recess 926 of the track 911, and the adjustable pin assembly 905 is moved into the first configuration by pressing the adjustable pin assembly 905 that extends from the bottom surface 950 of the handle 906. The details of the adjustable pin assembly 905 are further explained with reference to FIGS. 10-12.

Figure 10:
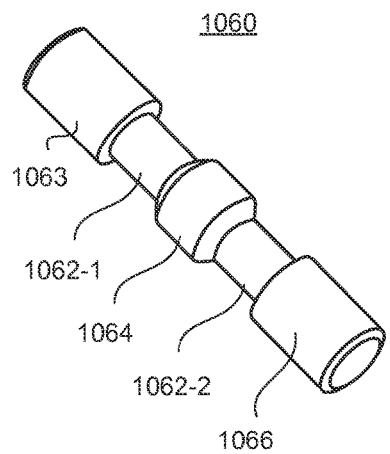
FIG. 10 illustrates an example of a modified pin.
Figure 11:
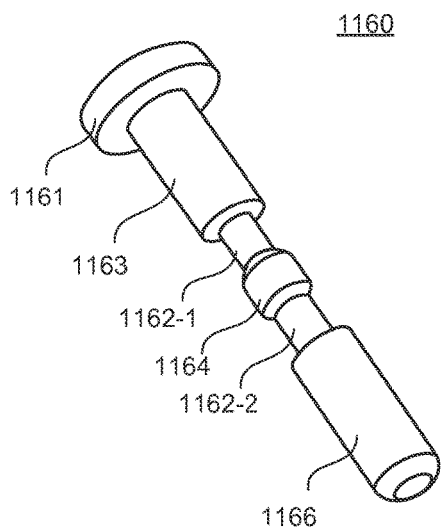
FIG. 11 illustrates an example of a modified pin.
Figure 12:
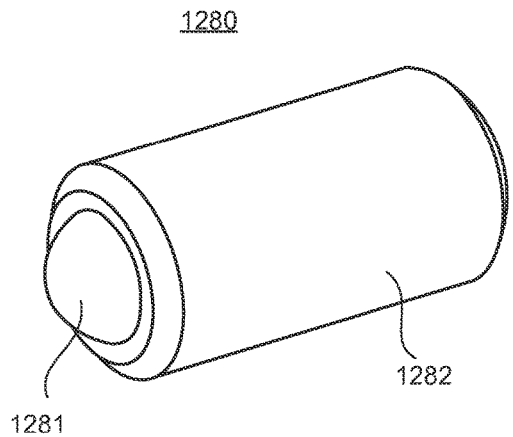
FIG. 12 illustrates a spring-loaded ball detent.

In some examples, the adjustable pin assembly 905 may include a modified pin and a spring-loaded detent. In some example, the pin 805 of FIGS. 8A-8F is modified with reduced diameter portions 1062. The modified pin and the spring-loaded detent may enable the first configuration and the second configuration to be semi-locked (e.g. a first semi-locked position and a second semi-locked position). In some examples, the semi-locked positions may be considered bi-stable. In other words, the first configuration and the second configuration are semi-locked in the sense that the modified pin is switchable between the first configuration and the second configuration, but when the modified pin is in either the first configuration or the second configuration, the modified pin is relatively stable. FIG. 10 illustrates an example of a modified pin 1060 according to an aspect. FIG. 11 illustrates an example of a modified pin 1160 according to another aspect. FIG. 12 illustrates a spring-loaded ball detent 1280 according to an aspect.

Referring to FIG. 10, the modified pin 1060 may be an elongated tubular structure. The modified pin 1060 may include a first reduced diameter portion 1062-1 and a second reduced diameter portion 1062-1. For example, the reduced diameter portions 1062 may have a diameter less than the diameter of other portions of the modified pin 1060. In some examples, the first reduced diameter portion 1062-1 may be disposed a distance from the second reduced diameter portion 1062-2.

The modified pin 1060 may define a first end portion 1063, a middle portion 1064, and a second end portion 1066. The diameter of the first end portion 1063, the middle portion 1064, and the second end portion 1066 may be greater than the diameter of the reduced diameter portions 1062. The first reduced diameter portion 1062-1 may be disposed between the first end portion 1063 and the middle portion 1064. The second reduced diameter portion 1062-1 may be disposed between the middle portion 1064 and the second end portion 1066. In some examples, the middle portion 1064 may separate the first reduced diameter portion 1062-1 from the second reduced diameter portion 1062-1. In some examples, the first end portion 1063 may have a length equal to the second end portion 1066. In other examples, the first end portion 1063 has a different length. In some examples, the middle portion 1064 may have a length shorter than the length of the first end portion 1063 and the second end portion 1066. In some examples, the middle portion 1064 may have tapered edge portions that taper towards the first reduced diameter portion 1062-1 and the second reduced diameter portion 1062-2.

In FIG. 11, the modified pin 1160 may include the same components as the modified pin 1060 of FIG. 10 except the modified pin 1160 of FIG. 11 includes a head portion 1161. For example, the modified pin 1160 may include a first end portion 1163, a first reduced diameter portion 1162-1, a middle portion 1164, a second reduced diameter portion 1162-2, and a second end portion 1166. Because these components were previously described with reference to FIG. 10, the description of these components is omitted for the sake of brevity. The head portion 1161 may have a diameter larger than the diameters of the first end portion 1163, the first reduced diameter portion 1162-1, the middle portion 1164, the second reduced diameter portion 1162-2, and the second end portion 1166.

In FIG. 12, the spring-loaded ball detent 1280 may include a tubular structure 1282 and a ball 1281. The tubular structure 1282 contains a spring (not shown) and partially encloses the ball 1281. For example, a portion of the ball 1281 may protrude out of one end of the tubular structure 1282. The spring within the tubular structure exerts a force on a portion of the ball 1281 disposed within the tubular structure such that a portion of the ball 1281 protrudes out of the tubular structure 1282. However, when a force (opposite to the spring) is applied to the ball 1281, the ball 1281 is configured to retreat into the tubular structure 1282. It is noted that other types of spring-loaded detents can be used with the modified pins of FIGS. 10 and 11.

Figure 13A:
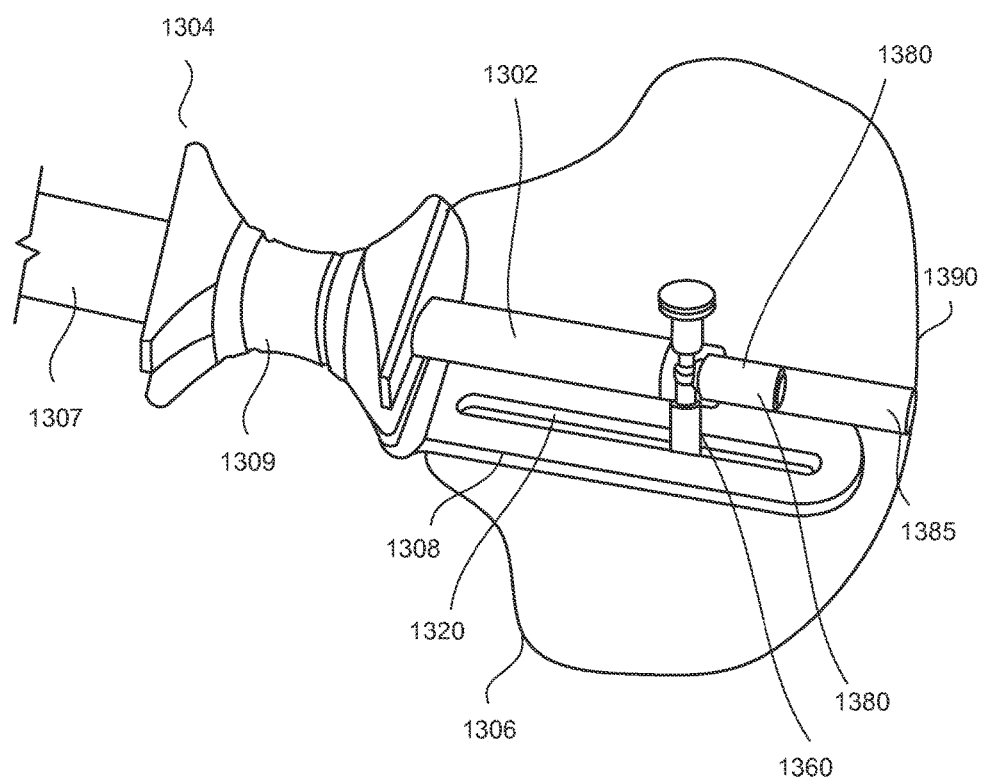
FIG. 13A illustrates a perspective of the spring-loaded detent and the modified pin.
Figure 13B:
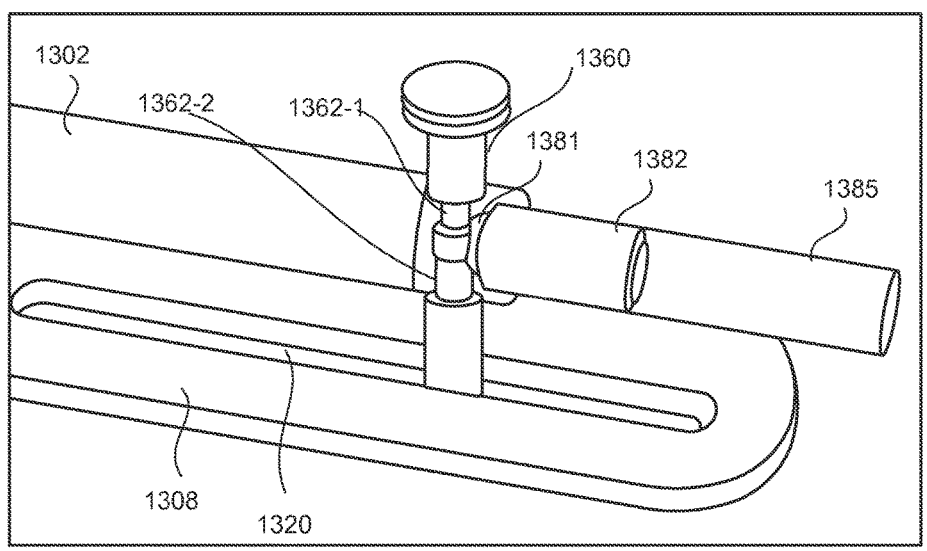
FIG. 13B illustrates a more detailed perspective of the spring-loaded detent and the modified pin.

FIGS. 13A-13B illustrate a medical device 1300 depicting the interaction of a spring-loaded detent 1380 and a modified pin 1360 within a handle 1306 in order to provide the modified pin 1360 with a first semi-locked position and a second semi-locked position. FIG. 13A illustrates a perspective of the spring-loaded detent 1380 and the modified pin 1360 according to an aspect. FIG. 13B illustrates a more detailed perspective of the spring-loaded detent 1380 and the modified pin 1360.

The medical device 1300 may include the spring-loaded detent 1380, the modified pin 1360, a needle member 1302 coupled to the handle 1306, and a pusher member 1304 having a sheath 1307, a handle portion 1309, and an extension member defining a slot 1320. The modified pin 1360 may be the modified pin 1060 of FIG. 10 or the modified pin 1160 of FIG. 11. The modified pin 1360 may include a first reduced diameter portion 1362-1 and a second reduced diameter portion 1362-2. The spring-loaded detent 1380 may be the spring-loaded ball detent 1280 of FIG. 12. For example, the spring-loaded detent 1380 may include a ball 1381 and a tubular structure 1382.

The handle 1306 may define a cavity 1385 on the rear surface 1390 of the handle 1306. For example, the cavity 1385 may have an opening on the rear surface 1390 of the handle 1306 and may linearly extend into the handle 1306. The spring-loaded detent 1380 may be inserted into the handle 1306 through the cavity 1385. In some examples, after the spring-loaded detent 1380 is inserted, the cavity 1385 may be filled with a permanent medium (e.g., epoxy) or an insert. The ball 1381 of the spring-loaded detent 1380 may be facing the distal direction.

As discussed in FIGS. 9A-9D, the handle 1306 may define a through-hole that extends from the surface within the recess of the handle 1306 to the bottom surface of the handle 906. For example, one opening of the through-hole is disposed within the recess, and the other opening of the through-hole is disposed on the bottom surface. The modified pin 1360 may be inserted into the through-hole of the handle 1306 such that the spring-loaded detent 1380 and the modified pin 1360 are perpendicular to each other.

The interaction of the spring-loaded detent 1380 and the modified pin 1360 (e.g., the interaction of the spring-loaded detent 1380 with the two reduced diameter portions 1362) may provide the modified pin 1360 with the first semi-locked position and the second semi-locked position. For example, in the first semi-locked position, the ball 1381 of the spring-loaded detent 1380 is disposed in the second reduced diameter portion 1362-1. In the second semi-locked position, the ball 1381 of the spring-loaded detent 1380 is disposed in the first reduced diameter portion 1362-1. The larger diameter portions (e.g., the first end portion, the middle portion, and the second end portion) that surround the reduced diameter portions 1362 assist in keeping the modified pin 1360 in the first and second semi-locked positions. When the modified pin 1360 transitions from the first semi-locked position to the second semi-locked position (or vice versa), the ball 1381 of the spring-loaded detent 1380 is pushed into the tubular structure 1382 due to the force applied on the ball 1381 by the middle portion of the modified pin 1360. In this context, the tapered edge portions of the middle portion of the modified pin 1360 may facilitate the transition from the first semi-locked position to the second semi-locked position (or vice versa). These positions may be semi-locked in the sense that the modified pin 1360 is switchable among the positions, but when the modified pin 1360 is in either the first semi-locked position or the second semi-locked position, the modified pin 1360 is relatively stable.

Figure 14:
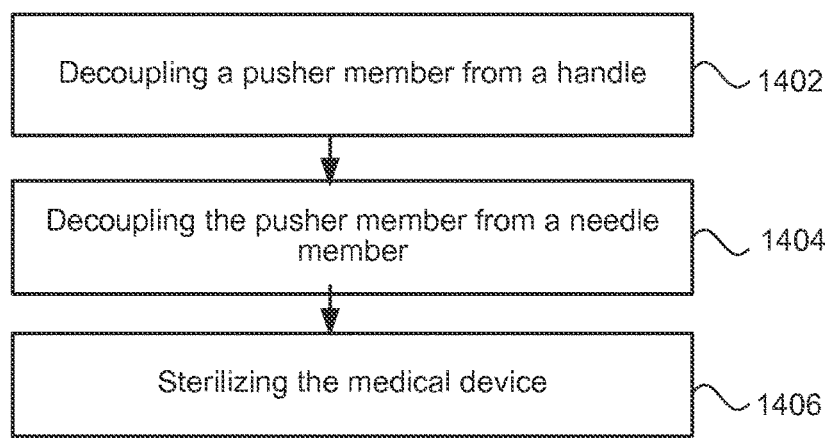
FIG. 14 illustrates a flowchart for a method of re-using a medical device.

FIG. 14 illustrates a flowchart 1400 for a method of re-using a medical device according to an aspect. For example, after the medical device is used within a surgical procedure, the following steps may be performed to help to disassemble the medical device to permit the medical device to be re-used. The medical device may be any of the medical devices described herein. For example, the medical device may include a pusher member, a needle member, a handle coupled to the needle member, and a protrusion component configured to protrude into a track of the handle. The pusher member may include a sheath, a handle portion, and an extension portion.

In step 1402, the pusher member may be de-coupled from the handle. In some examples, the pusher member may be moved to its extended position. Then, additional distal force may be applied on the pusher member to permit the enlarged position of the extension member to slide over the protrusion component. In some examples, the protrusion component may be any of the inserts discussed in FIGS. 1 and 6-7. In some examples, the protrusion component may be any of the protrusion components discussed in FIGS. 1-5. In other examples, the protrusion component may be adjustable to permit the pusher member to be decoupled from the handle. In some examples, the protrusion component may be any of the pins discussed in FIGS. 1 and 8. For example, the pin may be removed from the handle thereby allowing the pusher member to be de-coupled from the handle. In other examples, the protrusion component may be any of the adjustable pin assemblies discussed in FIGS. 1 and 9-13. For example, the adjustable pin assembly may include a modified pin that is moved such that no portion of the modified pin is within the track, thereby permitting the pusher member to be decoupled from the handle.

In step 1404, the pusher member may be decoupled from the needle member. In some examples, the sheath of the pusher member may be bendable such that when sliding the pusher member over a curved or bent needle member, the sheath bends to the curvature of the needle member to allow the pusher member to be removed from the distal end portion of the needle member, as discussed in FIGS. 1-4. In other examples, the pusher member may define a slot, and the pusher member may be decoupled from the needle member via the slot, as discussed in FIGS. 1 and 5-13. In step 1406, the medical device may be sterilized such that the medical device can be re-assembled and then used in a subsequent medical procedure.

According to an aspect, a medical device includes a needle member having a curved portion, a handle coupled to the needle member, and a pusher member including a sheath and an extension member. The extension member is configured to be slidably coupled to a track of the handle such that extension member slides within the track during a medical procedure. The sheath defines a lumen configured to receive a portion of the needle member. The extension member is configured to be de-coupled from the track of the handle after the medical procedure. The sheath is configured to be de-coupled from the needle member after the medical procedure.

In some examples, the medical device may include a protrusion component configured to be coupled to the handle. The protrusion component is configured to limit movement of the pusher member in relation to the handle during the medical procedure. In some examples, the protrusion component includes an insert having a base and a flexible projection that extends from the base, where the insert is configured to be inserted into a slot of the handle such that, when inserted, the flexible projection protrudes into the track of the handle. In other examples, the protrusion component includes an insert having a flexible projection, where the insert is being coupled to the track of the handle. In some examples, the protrusion component includes a removable pin, and the handle defines a through-hole configured to receive the removable pin such that a portion of the removable pin protrudes into the track of the handle. In some examples, the protrusion component includes an adjustable pin assembly having a modified pin and a spring-loaded detent.

In some examples, the extension member defines a slot. In some examples, the shaft is a bendable shaft, where the bendable sheath of the pusher member is configured to conform to the curved portion when the bendable sheath of the pusher member is moved over the curved portion of the needle member. In some example, the bendable shaft defines a plurality of recesses.

According to aspects, a method for enabling reuse of a medical device having a pusher member, a needle member having a curved portion, and a handle, includes decoupling an extension member of the pusher member from a track of the handle after a medical procedure, decoupling the pusher member from the needle member, and sterilizing the pusher member, the needle member, and the handle.

In some examples, the handle includes a protrusion disposed within the track of the handle configured to limit distal movement of the pusher member during the surgical procedure, and the decoupling the extension member of the pusher member from the track of the handle includes applying greater distal force to the extension member than applied during the medical procedure to slide the extension member past the protrusion. In some examples, the decoupling the extension member of the pusher member from the track of the handle includes moving the protrusion such that the protrusion does not extend within the track of the handle and moving the pusher member in a distal direction such that the extension member is not disposed with the track of the handle. In some examples, the decoupling the pusher member from the needle member includes sliding the pusher member over the curved portion of the needle member such that a bendable sheath of the pusher member conforms to a curvature of the curved portion of the needle member. In some examples, the pusher member defines a slot extending along a longitudinal axis of the pusher member, and the decoupling the pusher member from the needle member includes decoupling the pusher member from the needle member via the slot. In some examples, coupling the pusher member to the needle member includes sliding a distal end portion of the needle member into a lumen of the pusher member and coupling the extension member of the pusher member to the track of the handle such that the extension member can slide within the track of the handle.

According to an aspect, a medical device may include a needle member having a curved portion, a handle coupled to the needle member, and a pusher member including a bendable sheath and an extension member. The extension member is configured to be slidably coupled to a track of the handle such that extension member slides within the track during a medical procedure. The bendable sheath defines a lumen configured to receive a portion of the needle member. The extension member is configured to be de-coupled from the track of the handle after the medical procedure. The bendable sheath is configured to be de-coupled from the needle member after the medical procedure. The bendable sheath of the pusher member is configured to conform to the curved portion when the bendable sheath of the pusher member is moved over the curved portion of the needle member.

In some examples, a protrusion component is configured to be coupled to the handle, where the protrusion component configured to limit movement of the pusher member in relation to the handle during the medical procedure. In some examples, the protrusion component includes an insert having a base and a flexible projection that extends from the base, where the insert configured to be inserted into a slot of the handle such that, when inserted, the flexible projection protrudes into the track of the handle. In other examples, the protrusion component includes an insert having a flexible projection, where the insert is coupled to the track of the handle.

In some examples, the protrusion component includes a removable pin, and the handle defines a through-hole configured to receive the removable pin such that a portion of the removable pin protrudes into the track of the handle. In some examples, the protrusion component includes an adjustable pin assembly including a modified pin and a spring-loaded detent. The extension member may define a slot. The bendable shaft may include a plurality of recesses. The extension member may define an enlarged portion of a proximal end of the extension member.

According to an aspect, a medical device may include a needle member, a handle coupled to the needle member, and a pusher member including a sheath and an extension member. The extension member is configured to be slidably coupled to a track of the handle such that extension member slides within the track during a medical procedure. The sheath defines a lumen configured to receive a portion of the needle member. The pusher member is configured to be de-coupled from the handle. The medical device includes a protrusion component configured to be coupled to the track of the handle, where the protrusion component is configured to protrude into the track of the handle such that a travel distance of the pusher member is limited.

In some examples, the needle member includes a curved portion, and sheath is bendable such that the sheath is configured to bend over the curved portion of the needle member when decoupling the pusher member from the needle member. In some examples, the pusher member defines a slot such that the pusher member is configured to be de-coupled from the needle member via the slot.

In some examples, the protrusion component includes an insert having a base and a flexible projection that extends from the base, and the insert is configured to be inserted into a slot of the handle such that, when inserted, the flexible projection protrudes into the track of the handle. In other examples, the protrusion component includes an insert having a flexible projection, and the insert is coupled to the track of the handle. In some examples, the protrusion component includes a removable pin, and the handle defines a through-hole configured to receive the removable pin such that a portion of the removable pin protrudes into the track of the handle. In some examples, the protrusion component is adjustable between a first semi-locked position and a second semi-locked position. The extension member may define a slot.

According to an aspect, a medical device may include a needle member, a handle coupled to the needle member, and a pusher member including a sheath and an extension member. The extension member is configured to be slidably coupled to a track of the handle such that extension member slides within the track during a medical procedure. The sheath defines a lumen configured to receive a portion of the needle member. The pusher member is configured to be de-coupled from the handle. The pusher member is configured to be de-coupled from the handle. The medical device includes a protrusion component configured to be coupled to the track of the handle, and the protrusion includes an insert configured to be inserted into a slot of the handle such that, when inserted, the insert is configured to protrude into the track of the handle to limit a travel distance of the pusher member. In some examples, the insert is removable after the medical procedure. In other examples, the insert is not removable after the medical procedure.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A medical device comprising:
   a needle member having a curved portion;
   a handle coupled to the needle member, the handle having a first outer surface and a second outer surface disposed opposite the first outer surface, the handle defining a track disposed on the first outer surface, the handle defining a through-hole extending from the second outer surface to the track; and
   a pusher member including a bendable sheath and an extension member, the extension member configured to be slidably coupled to the track of the handle such that the extension member slides within the track during a medical procedure, the bendable sheath defining a lumen configured to receive a portion of the needle member, the extension member configured to be de-coupled from the track of the handle after the medical procedure, the bendable sheath configured to be de-coupled from the needle member after the medical procedure, the bendable sheath of the pusher member configured to conform to the curved portion when the bendable sheath of the pusher member is moved over the curved portion of the needle member.

2. The medical device of claim 1, further comprising:
   a protrusion component configured to be coupled to the handle, the protrusion component configured to limit movement of the pusher member in relation to the handle during the medical procedure.

3. The medical device of claim 2, wherein the protrusion component includes an insert having a base and a flexible projection that extends from the base, the insert configured to be inserted into a slot of the handle such that, when inserted, the flexible projection protrudes into the track of the handle.

4. The medical device of claim 2, wherein the protrusion component includes an insert having a flexible projection, the insert being coupled to the track of the handle.

5. The medical device of claim 2, wherein the protrusion component includes a removable pin, the through-hole configured to receive the removable pin such that a portion of the removable pin protrudes into the track of the handle.

6. The medical device of claim 2, wherein the protrusion component includes an adjustable pin assembly including a modified pin and a spring-loaded detent.

7. The medical device of claim 1, wherein the extension member defines a slot.

8. The medical device of claim 1, wherein the bendable sheath includes a plurality of recesses.

9. The medical device of claim 1, wherein the extension member defines an enlarged portion of a proximal end of the extension member.

10. A medical device comprising:
a needle member;
a handle coupled to the needle member;
a pusher member including a sheath and an extension member, the extension member configured to be slidably coupled to a track of the handle such that the extension member slides within the track during a medical procedure, the extension member includes a first leg and a second leg that is spaced apart from the first leg, the space between the first leg and the second leg defining an opening, the extension member further includes a joining portion that connects the first leg and the second leg and configured to slide within the track, the sheath defining a lumen configured to receive a portion of the needle member, the pusher member defines a slot extending from a first end portion of the pusher member to a second end portion of the pusher member opposite the first end portion, the pusher member configured to be de-coupled from the needle member via the slot; and
a protrusion component configured to be coupled to the track of the handle, the protrusion component configured to protrude into the track of the handle such that a travel distance of the pusher member is limited.

11. The medical device of claim 10, wherein the needle member includes a curved portion, and the sheath is bendable such that the sheath is configured to bend over the curved portion of the needle member when decoupling the pusher member from the needle member.

12. The medical device of claim 10, wherein the protrusion component includes an insert having a base and a flexible projection that extends from the base, the insert configured to be inserted into a slot of the handle such that, when inserted, the flexible projection protrudes into the track of the handle.

13. The medical device of claim 10, wherein the protrusion component includes an insert having a flexible projection, the insert being coupled to the track of the handle.

14. The medical device of claim 10, wherein the protrusion component includes a removable pin, the handle defining a through-hole configured to receive the removable pin such that a portion of the removable pin protrudes into the track of the handle.

15. The medical device of claim 10, wherein the protrusion component is adjustable between a first semi-locked position and a second semi-locked position.

16. The medical device of claim 10, wherein the extension member defines a slot.

17. A medical device comprising:
a needle member;
a handle coupled to the needle member;
a pusher member including a sheath and an extension member, the extension member configured to be slidably coupled to a track of the handle such that the extension member slides within the track during a medical procedure, the extension member including a first leg and a second leg that is spaced apart from the first leg to define an opening, the extension member further including a joining portion that connects the first leg and the second leg and configured to slide within the track, the sheath defining a lumen configured to receive a portion of the needle member, the pusher member configured to be de-coupled from the handle; and
a protrusion component configured to be coupled to the track of the handle, the protrusion component including an insert configured to be inserted into the opening of the extension member such that, when inserted, the insert is configured to protrude into the track of the handle to limit a travel distance of the pusher member, the protrusion component including a screw member.

18. The medical device of claim 17, wherein the insert is removable after the medical procedure.

19. The medical device of claim 17, wherein the insert is not removable after the medical procedure.

* * * * *